United States Patent
Yamamoto et al.

(10) Patent No.: US 10,591,331 B2
(45) Date of Patent: Mar. 17, 2020

(54) INTAKE TEMPERATURE DETECTION DEVICE AND MAXIMUM HEAT GENERATING AMOUNT COMPONENTS MOUNTED ON A SINGLE CIRCUIT BOARD

(71) Applicant: Hitachi Automotive Systems, Ltd., Hitachinaka-shi, Ibaraki (JP)

(72) Inventors: Takahiro Yamamoto, Hitachinaka (JP); Hiroaki Hoshika, Hitachinaka (JP); Takayuki Yogo, Hitachinaka (JP); Takahiro Miki, Hitachinaka (JP); Takeo Hosokawa, Hitachinaka (JP); Yuki Isoya, Hitachinaka (JP)

(73) Assignee: Hitachi Automotive Systems, Ltd., Hitachinaka-shi (JP)

( * ) Notice: Subject to any disclaimer, the term of this patent is extended or adjusted under 35 U.S.C. 154(b) by 109 days.

(21) Appl. No.: 15/741,554

(22) PCT Filed: Aug. 3, 2016

(86) PCT No.: PCT/JP2016/072720
§ 371 (c)(1),
(2) Date: Jan. 3, 2018

(87) PCT Pub. No.: WO2017/056700
PCT Pub. Date: Apr. 6, 2017

(65) Prior Publication Data
US 2018/0372520 A1    Dec. 27, 2018

(30) Foreign Application Priority Data
Sep. 30, 2015    (JP) .................................. 2015-192505

(51) Int. Cl.
*G01F 1/684*    (2006.01)
*G01F 1/68*    (2006.01)
(Continued)

(52) U.S. Cl.
CPC ........... *G01F 1/6842* (2013.01); *F02D 41/18* (2013.01); *G01F 1/68* (2013.01); *G01F 1/684* (2013.01);
(Continued)

(58) Field of Classification Search
CPC ................. F02D 41/1493; F02D 41/19; F02D 2200/0418; G01M 15/04; G01F 1/684;
(Continued)

(56) References Cited

U.S. PATENT DOCUMENTS 6,552,441 B1 * 4/2003 Gander ............... B60R 16/0239
307/10.1
7,207,314 B2    4/2007 Sakurai et al.
(Continued)

FOREIGN PATENT DOCUMENTS

CN    102538867 A    7/2012
CN    102602263 A    7/2012
(Continued)

OTHER PUBLICATIONS

Chinese-language Office Action issued in counterpart Chinese Application No. 201680053895.2 dated May 7, 2019 with English translation (15 pages).
(Continued)

*Primary Examiner* — Harshad R Patel
*Assistant Examiner* — Nigel H Plumb
(74) *Attorney, Agent, or Firm* — Crowell & Moring LLP

(57) ABSTRACT

The present invention reduces, by optimizing disposition of components on an electronic circuit board, heat transfer from other components mounted on the same board, and improves measurement accuracy of an intake air temperature detection element. A physical quantity detection device of the present invention has an electronic circuit board, which is provided with one or more intake air temperature
(Continued)

detection elements (elements having intake air temperature detection function), and which processes electric signals. Furthermore, the physical quantity detection device has a configuration wherein the intake air temperature detection elements, and a power supply regulator having the maximum heat generation quantity are mounted on the same electronic circuit board. The physical quantity detection device is characterized in that the intake air temperature detection elements are disposed on the air flow upstream side of the power supply regulator.

6 Claims, 38 Drawing Sheets

(51) Int. Cl.
    *F02D 41/18*    (2006.01)
    *G01F 1/688*    (2006.01)
    *G01F 5/00*    (2006.01)
    *G01K 1/16*    (2006.01)
    *G01K 13/02*    (2006.01)
    *G01N 25/56*    (2006.01)
    *G01N 27/12*    (2006.01)

(52) U.S. Cl.
    CPC ............... *G01F 1/688* (2013.01); *G01F 5/00* (2013.01); *G01K 1/16* (2013.01); *G01K 13/02* (2013.01); *G01N 25/56* (2013.01); *G01N 27/121* (2013.01); *F02D 2200/0418* (2013.01); *G01K 2205/02* (2013.01)

(58) Field of Classification Search
    CPC .......... G01F 1/6842; G01F 1/68; G01F 1/688; G01F 5/00; G01K 1/16; G01K 13/02; G01K 2205/02; G01N 25/56; G01N 27/121
    See application file for complete search history.

(56) References Cited

U.S. PATENT DOCUMENTS

| | | | | |
|---|---|---|---|---|
| 8,806,933 | B2* | 8/2014 | Kohno | G01F 1/699 73/204.15 |
| 2004/0042527 | A1* | 3/2004 | Block | G01K 3/06 374/29 |
| 2008/0148842 | A1 | 6/2008 | Oda | |
| 2008/0163683 | A1 | 7/2008 | Becke et al. | |
| 2010/0296009 | A1 | 11/2010 | Shinki et al. | |
| 2011/0072894 | A1* | 3/2011 | Saito | F02D 41/187 73/114.34 |
| 2012/0085324 | A1* | 4/2012 | Saito | F02M 35/10393 123/494 |
| 2012/0160024 | A1* | 6/2012 | Matsumoto | G01F 1/6842 73/204.11 |
| 2014/0172280 | A1* | 6/2014 | Ogata | G01H 17/00 701/111 |
| 2014/0340846 | A1* | 11/2014 | Kurita | H05K 7/20145 361/695 |

FOREIGN PATENT DOCUMENTS

| | | |
|---|---|---|
| CN | 102607738 A | 7/2012 |
| CN | 204044137 U | 12/2014 |
| CN | 104344857 A | 2/2015 |
| DE | 195 04 572 A1 | 8/1996 |
| DE | 198 02 045 A1 | 7/1999 |
| DE | 199 05 384 A1 | 8/2000 |
| EP | 1 342 909 A2 | 9/2003 |
| EP | 1 394 520 A1 | 3/2004 |
| EP | 2 472 236 A1 | 7/2012 |
| EP | 3 176 544 A1 | 6/2017 |
| EP | 3 176 546 A1 | 6/2017 |
| EP | 3 232 167 A1 | 10/2017 |
| EP | 3 267 161 A1 | 1/2018 |
| FR | 2 779 228 A1 | 12/1999 |
| JP | 5-52625 A | 3/1993 |
| JP | 2000-28411 A | 1/2000 |
| JP | 2002-62306 A | 2/2002 |
| JP | 2002-318147 A | 10/2002 |
| JP | 2006-234766 A | 9/2006 |
| JP | 2007-263117 A | 10/2007 |
| JP | 2008-157742 A | 7/2008 |
| JP | 2009-175230 A | 8/2009 |
| JP | 2011-75357 A | 4/2011 |
| JP | 2012-137456 A | 7/2012 |
| JP | 2014-225573 A | 12/2014 |

OTHER PUBLICATIONS

Extended European Search Report issued in counterpart European Application No. 16850877.8 dated Apr. 23, 2019 (six (6) pages).
Third Party Observation issued in counterpart European Application No. 16850877.8 dated Feb. 11, 2019 (three (3) pages).
European Office Action issued in European Patent Application No. 16850877.8 dated Sep. 5, 2018 (three (3) pages).
Communication pursuant to Rule 114(2) EPC issued in counterpart European Application No. 16850877.8 dated Oct. 30, 2018 (three pages).
European Communication pursuant to Rule 114(2) EPC issued in counterpart European Application No. 16850877.8 dated May 16, 2019 (three (3) pages).
European Communication pursuant to Rule 114(2) EPC issued in counterpart European Application No. 16850877.8 dated Jun. 12, 2019 (three (3) pages).
International Search Report (PCT/ISA/210) issued in PCT Application No. PCT/JP2016/072720 dated Nov. 22, 2016 with English translation (5 pages).
Japanese-language Written Opinion (PCT/ISA/237) issued in PCT Application No. PCT/JP2016/072720 dated Nov. 22, 2016 (4 pages).
Japanese-language Third-Party Observation issued in counterpart Japanese Application No. 2017-542983 dated Jun. 25, 2019 (eight (8) pages).
Japanese-language Office Action issued in counterpart Japanese Application No. 2017-542983 dated Nov. 5, 2019 with English translation (six (6) pages).

* cited by examiner

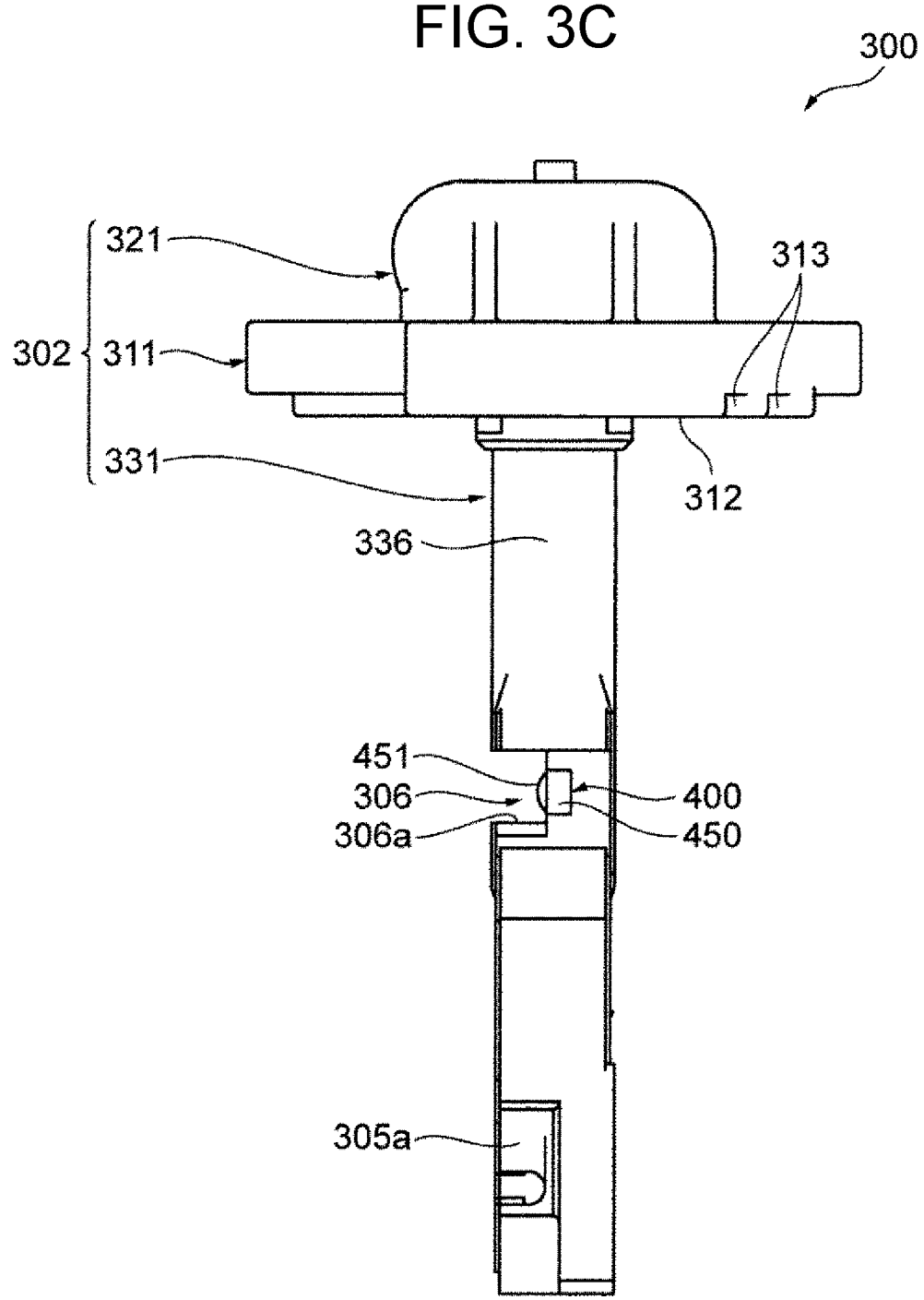

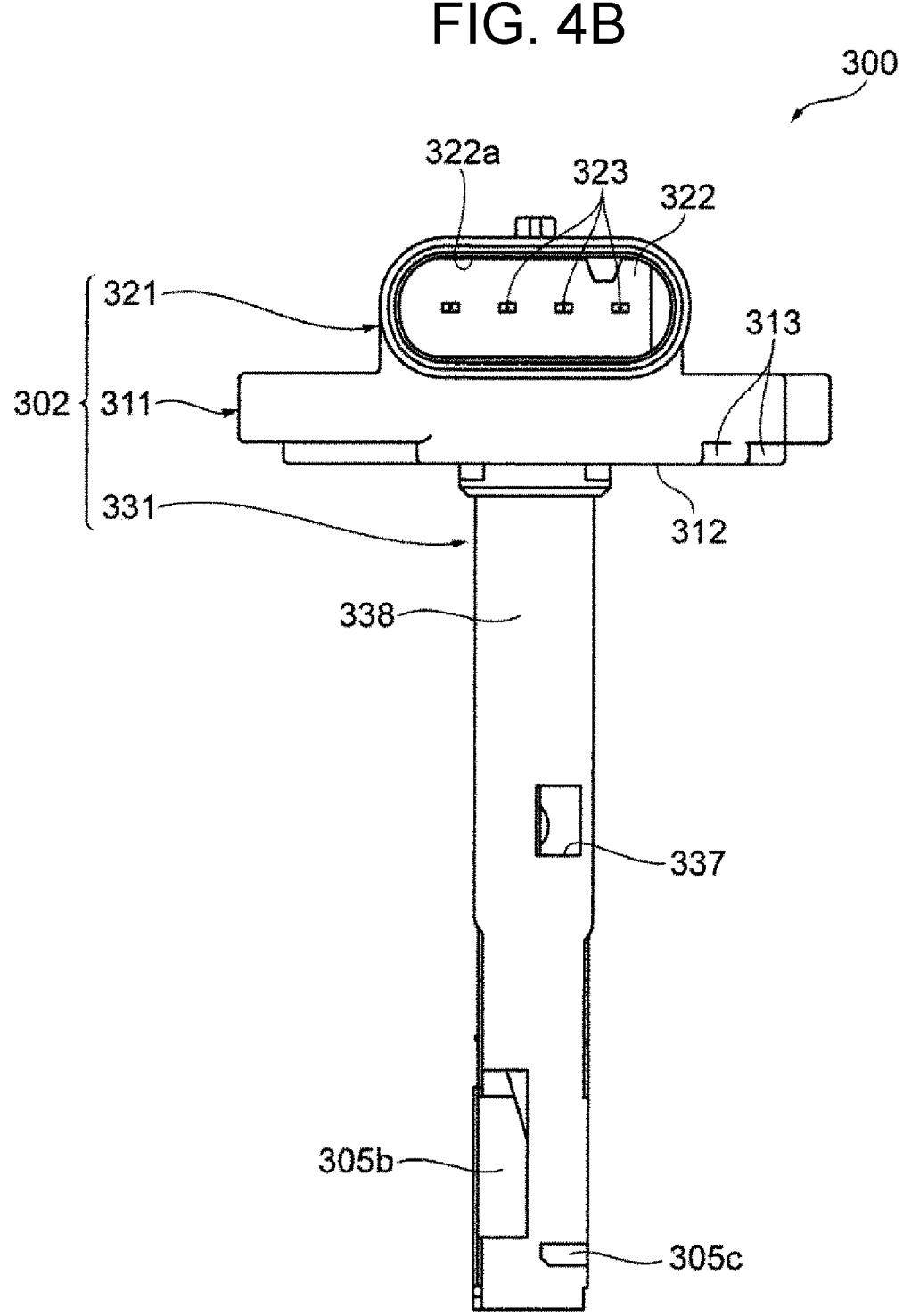

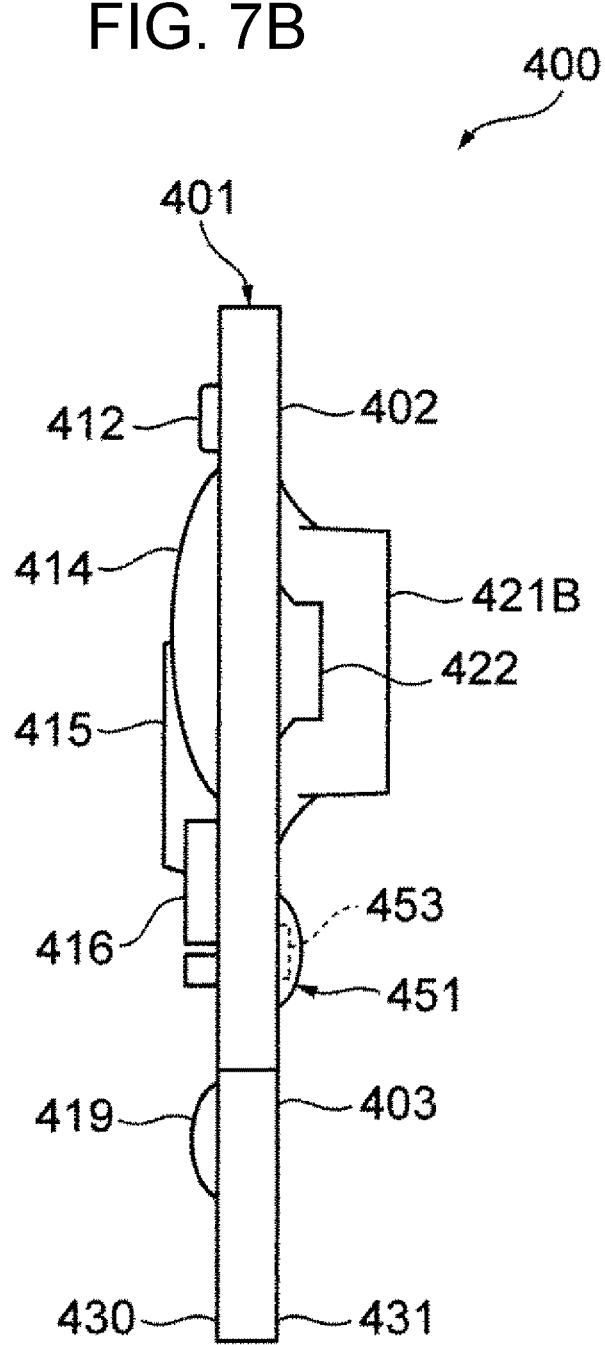

CROSS SECTION TAKEN ALONG LINE B-B

CROSS SECTION TAKEN ALONG LINE B-B

CROSS SECTION TAKEN ALONG LINE C-C

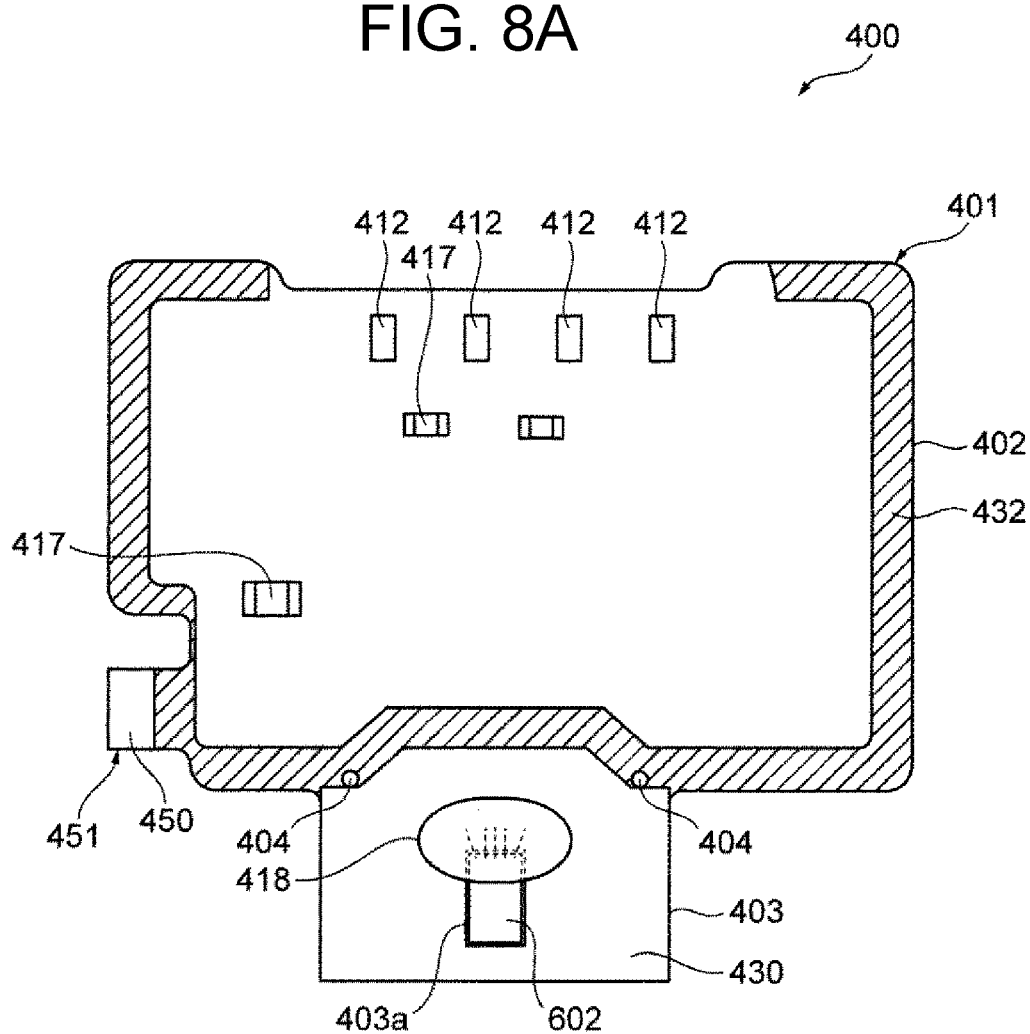

BEFORE CUTTING

AFTER CUTTING

INTAKE TEMPERATURE DETECTION DEVICE AND MAXIMUM HEAT GENERATING AMOUNT COMPONENTS MOUNTED ON A SINGLE CIRCUIT BOARD

TECHNICAL FIELD

The present invention relates to a physical quantity detection device of intake air of an internal combustion engine.

BACKGROUND ART

PTL 1 shows a structure in which a temperature measuring element is mounted on a sub air passage constituted by a part of a housing member, and a resin member constituting the sub-passage is formed with vent holes larger than the temperature measuring element on both side walls, and the temperature measuring element is disposed between the vent holes. In PTL 1, the temperature measuring element is installed at a position away from an electronic circuit board which drives the temperature measuring element.

CITATION LIST

Patent Literature

PTL 1: JP 2006-234766 A

SUMMARY OF INVENTION

Technical Problem

As shown in PTL 1, when the temperature measuring element and the driving circuit are not directly connected, the temperature measuring element and the driving circuit must be connected via a lead terminal or the like, which increases the number of assembling steps and the number of parts, leading to expansion of the module outer shape. On the other hand, in electronic circuit boards, the increase in the heat generation density is remarkable due to the high density mounting of many electronic components, and the circuit self heating causes a problem. Therefore, in a configuration in which a physical quantity detection element, a control IC, a power supply component, and the like are collectively mounted on the same circuit board, the influence of heat generation of other components is transmitted via the circuit board, so that the measurement accuracy of the physical quantity detection element is greatly affected. Therefore, it is necessary to reduce the circuit self-heating effect on the detection element.

The present invention has been made in view of the above issues, and it is an object of the present invention to provide a physical quantity detection device in which the heat transfer from other parts mounted on the same substrate is reduced by optimizing the arrangement of parts on the electronic circuit board, and in which the measurement accuracy of the intake temperature detection element is improved.

Solution to Problem

To solve the problem described above, a physical quantity detection device of the present invention includes one or more intake temperature detection elements and an electronic circuit board processing an electric signal, wherein the one or more intake temperature amount detection elements and a component having a maximum heat generation amount are configured to be mounted on the same electronic circuit board, and the one or more intake temperature detection elements are arranged at an air flow upstream portion with respect to the component having the maximum heat generation amount.

Advantageous Effects of Invention

According to the present invention, the heat transfer from other components mounted on the same substrate can be reduced by optimizing the arrangement of components on the electronic circuit board, and the measurement accuracy of the intake temperature detection element can be improved. The problems, configurations, and effects other than those described above will be clarified from the description of the following embodiments.

BRIEF DESCRIPTION OF DRAWINGS

FIG. 3C is a left side view showing a state in which the front cover and the back cover are removed from the physical quantity detection device.

FIG. 4B is a right side view of the housing shown in FIG. 4A.

FIG. 7B is a right side view of the circuit board.

FIG. 8A is a front view showing another embodiment of a circuit board.

DESCRIPTION OF EMBODIMENTS

Figure 1:
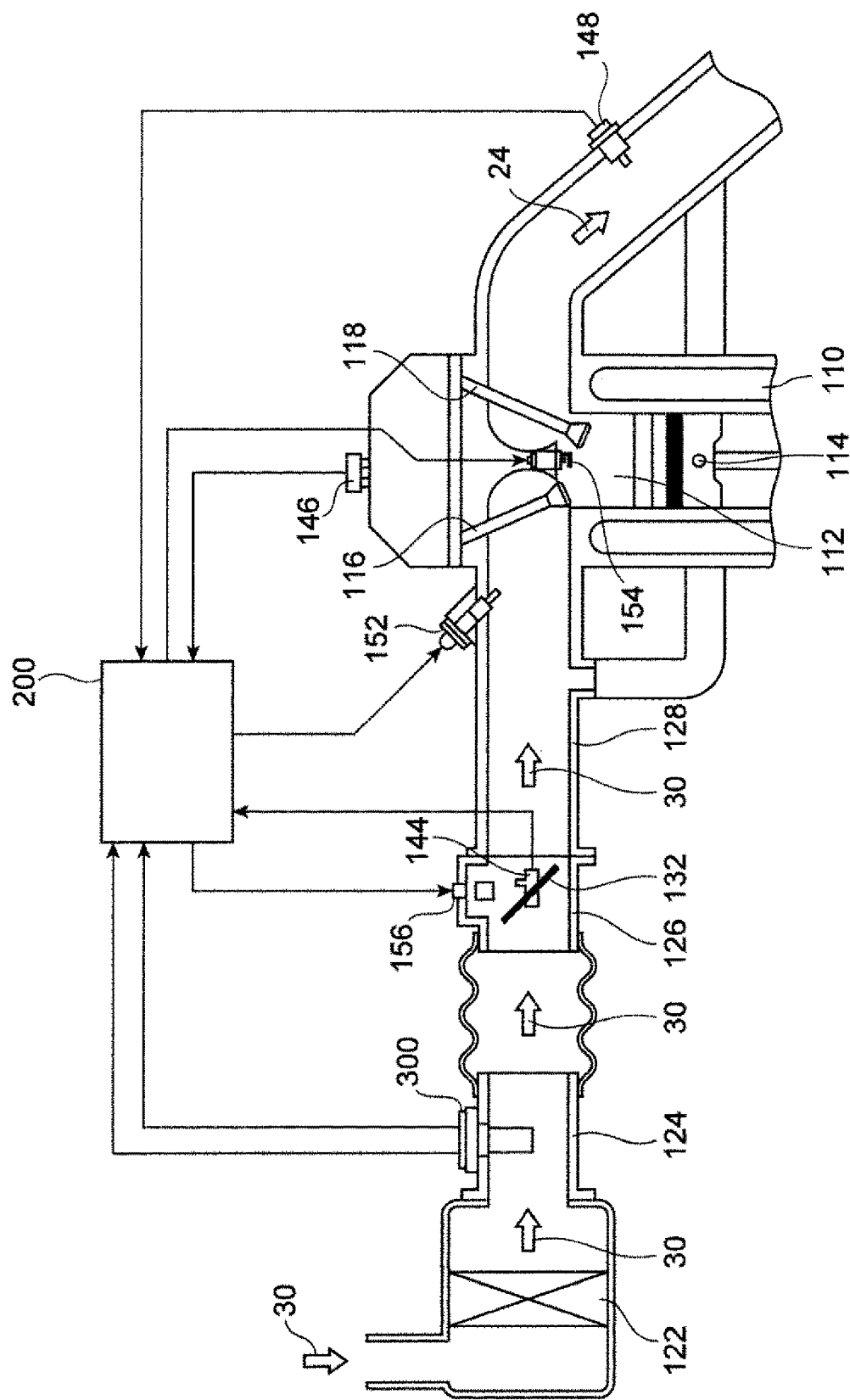
FIG. 1 is a system diagram showing an embodiment using a physical quantity detection device according to the present invention in an internal combustion engine control system.

A mode for carrying out the invention (hereinafter referred to as an embodiment) described below solves various problems which are demanded as actual products, and solves various problems desirable for use as a detection device for detecting a physical quantity of intake air, in particular, of a vehicle, and achieve various effects. One of various problems solved by the following embodiment is the contents described in the Technical Problem described above, and one of the various effects exhibited by the following embodiments is the effect described in Advantageous Effects of Invention. Various problems solved by the following embodiments and various effects which are exerted by the following examples will be described in the description of the following embodiments. Accordingly, the problems and effects solved by the embodiments described in the following embodiments are also described with regard to the contents other than the contents of the Technical Problem and the Advantageous Effects of Invention.

In the following embodiments, the same reference numerals indicate the same elements and achieve the same operational effect even if they are in different drawings. For the elements already described, only the reference symbols are given in the drawings, and the explanation thereabout may be omitted in some cases.

1. One Embodiment Using Physical Quantity Detection Device According to the Present Invention in Internal Combustion Engine Control System FIG. 1 is a system diagram showing an embodiment using the physical quantity detection device according to the present invention in an internal combustion engine control system of an electronic fuel injection method. Based on the operation of an internal combustion engine 110 having an engine cylinder 112 and an engine piston 114, the intake air is sucked from the air cleaner 122 as the measurement target gas 30, and is taken through the main passage 124, for example, an intake body, a throttle body 126, and an intake manifold 128 and is guided to a combustion chamber of the engine cylinder 112. The physical quantity of the measurement target gas 30 which is the intake air led to the combustion chamber is detected by a physical quantity detection device 300 according to the present invention. The fuel is supplied from the fuel injection valve 152 based on the detected physical quantity, and is led to the combustion chamber in an air-fuel mixture state with the intake air 20. In the present embodiment, the fuel injection valve 152 is provided in the intake port of the internal combustion engine, and the fuel injected into the intake port forms an air-fuel mixture with the measurement target gas 30 which is the intake air, and it is led to the combustion chamber via the intake valve 116 to be combusted to generate mechanical energy.

The fuel and the air led to the combustion chamber form a mixed state of fuel and air, and explosively burn due to spark ignition of a spark plug 154 to generate mechanical energy. The gas generated by the combustion is guided from an exhaust valve 118 to the exhaust pipe and discharged as exhaust gas 24 from the exhaust pipe to the outside of the vehicle. The flow rate of the measurement target gas 30, which is intake air led to the combustion chamber, is controlled by a throttle valve 132 of which opening degree varies on the basis of operation of an accelerator pedal. The fuel supply amount is controlled based on the flow rate of the intake air led to the combustion chamber. The driver can control the mechanical energy generated by the internal combustion engine by controlling the opening degree of the throttle valve 132 and controlling the flow rate of the intake air guided to the combustion chamber.

1.1 Overview of Control of Internal Combustion Engine Control System

The physical quantity such as the flow rate, temperature, humidity, pressure, and the like of the measurement target gas 30 which is taken in from the air cleaner 122 and flows through the main passage 124 is detected by the physical quantity detection device 300, and an electric signal representing the physical quantity of the intake air is input into the control device 200 from the physical quantity detection device 300. The output of the throttle angle sensor 144 for measuring the opening degree of the throttle valve 132 is input to the control device 200. Further, the position and the state of the engine piston 114 of the internal combustion engine, the intake valve 116, and the exhaust valve 118 are input to the control device 200, and further, in order to measure the rotation speed of the internal combustion engine, the output of the rotation angle sensor 146 is input to the control device 200. The output of the oxygen sensor 148 is input to the control device 200 in order to measure the state of the mixture ratio of the fuel quantity and the air quantity from the state of the exhaust gas 24.

Based on the physical quantity of the intake air which is the output of the physical quantity detection device 300 and the rotation speed of the internal combustion engine measured based on the output of the rotation angle sensor 146, the control device 200 calculates the fuel injection amount and the ignition timing. Based on these calculation results, the amount of fuel supplied from the fuel injection valve 152 and the ignition timing ignited by the spark plug 154 are controlled. The fuel supply amount and the ignition timing are actually controlled in details based on the temperature detected by the physical quantity detection device 300, the change state of the throttle angle, the change state of the engine rotation speed, and the state of the air fuel ratio measured by the oxygen sensor 148. The control device 200 further controls the amount of air bypassing the throttle valve 132 by an idle air control valve 156 in the idle operation state of the internal combustion engine, and controls the rotation speed of the internal combustion engine in the idle operation state.

1.2 Importance of Improving the Detection Accuracy of Physical Quantity Detection Device and Mounting Environment of Physical Quantity Detection Device Both the fuel supply amount and the ignition timing which are the main control amount of the internal combustion engine are calculated using the output of the physical quantity detection device 300 as the main parameter. Therefore, improvement of the detection precision of the physical quantity detection device 300, suppression of change over time, and improvement of reliability are important for improving the control precision of the vehicle and ensuring reliability.

Particularly in recent years, the demand for fuel saving of vehicles has been very high, and the demand for purification of exhaust gas is very high. In order to satisfy these demands, it is extremely important to improve the detection accuracy of the physical quantity of the intake air 20 detected by the physical quantity detection device 300. It is also important that the physical quantity detection device 300 maintains high reliability.

Vehicles equipped with the physical quantity detection device 300 are used in environments where the temperature and the humidity greatly change. It is desirable that the physical quantity detection device 300 is also designed to cope with changes in the temperature and the humidity in its use environment, and to deal with dust and contaminants.

The physical quantity detection device 300 is attached to an intake pipe which is affected by the heat generated from the internal combustion engine. Therefore, the heat generation of the internal combustion engine is transmitted to the physical quantity detection device 300 via the intake pipe which is the main passage 124. Since the physical quantity detection device 300 detects the flow rate of the measurement target gas by performing heat transfer with the measurement target gas, it is important to suppress the influence of heat from the outside as much as possible.

As described below, the physical quantity detection device 300 installed in the car not only solves the problem described in the Technical Problem and exhibits the effects described in Advantageous Effects of Invention but also, as explained below, takes various problems mentioned above into consideration, solves various problems required as products, and achieves various effects. Specific problems to be solved by the physical quantity detection device 300 and concrete effects achieved thereby will be described in the description of the following embodiments.

2. Configuration of Physical Quantity Detection Device 300

2.1 External Structure of Physical Quantity Detection Device 300

Figure 2A:
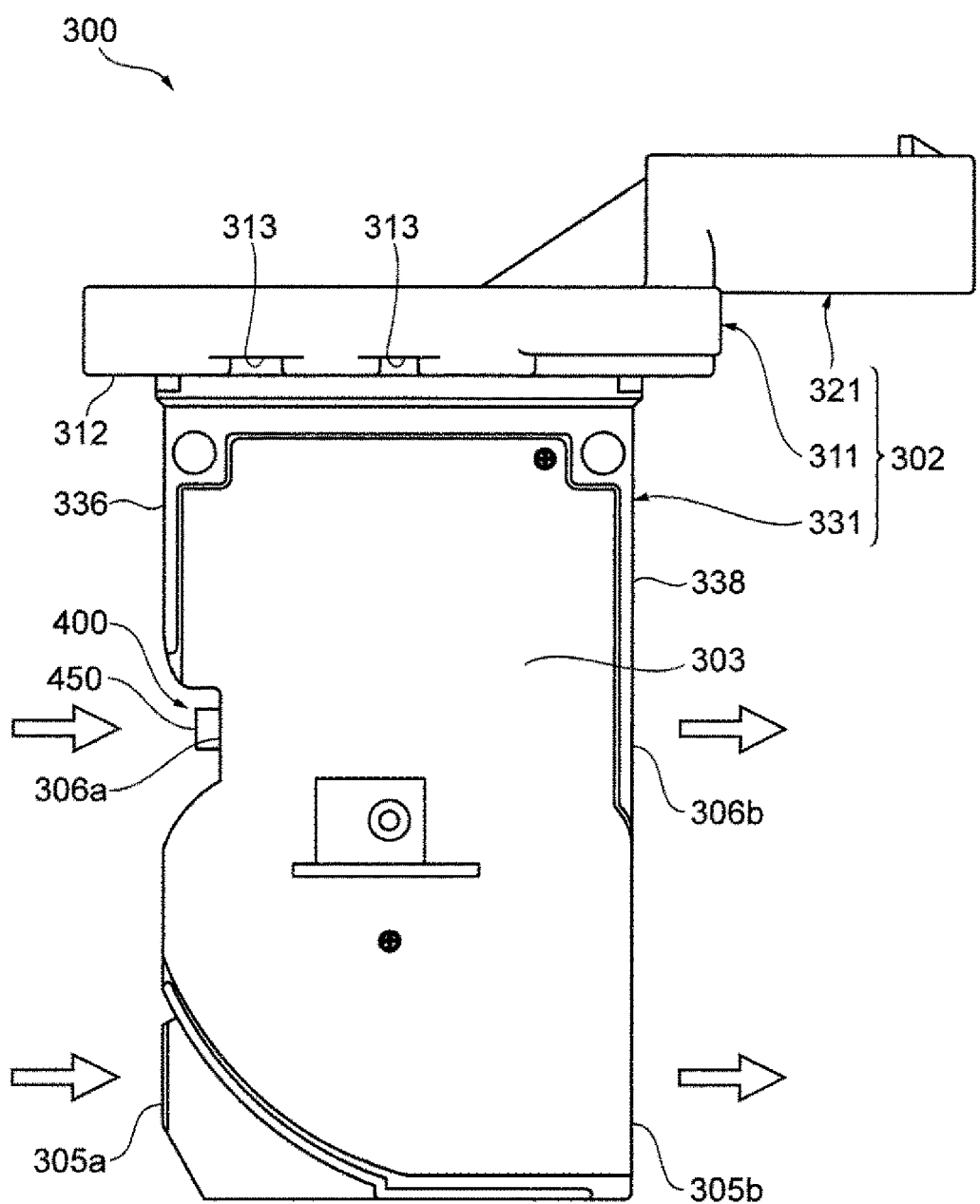
FIG. 2A is a front view of the physical quantity detection device.
Figure 2B:
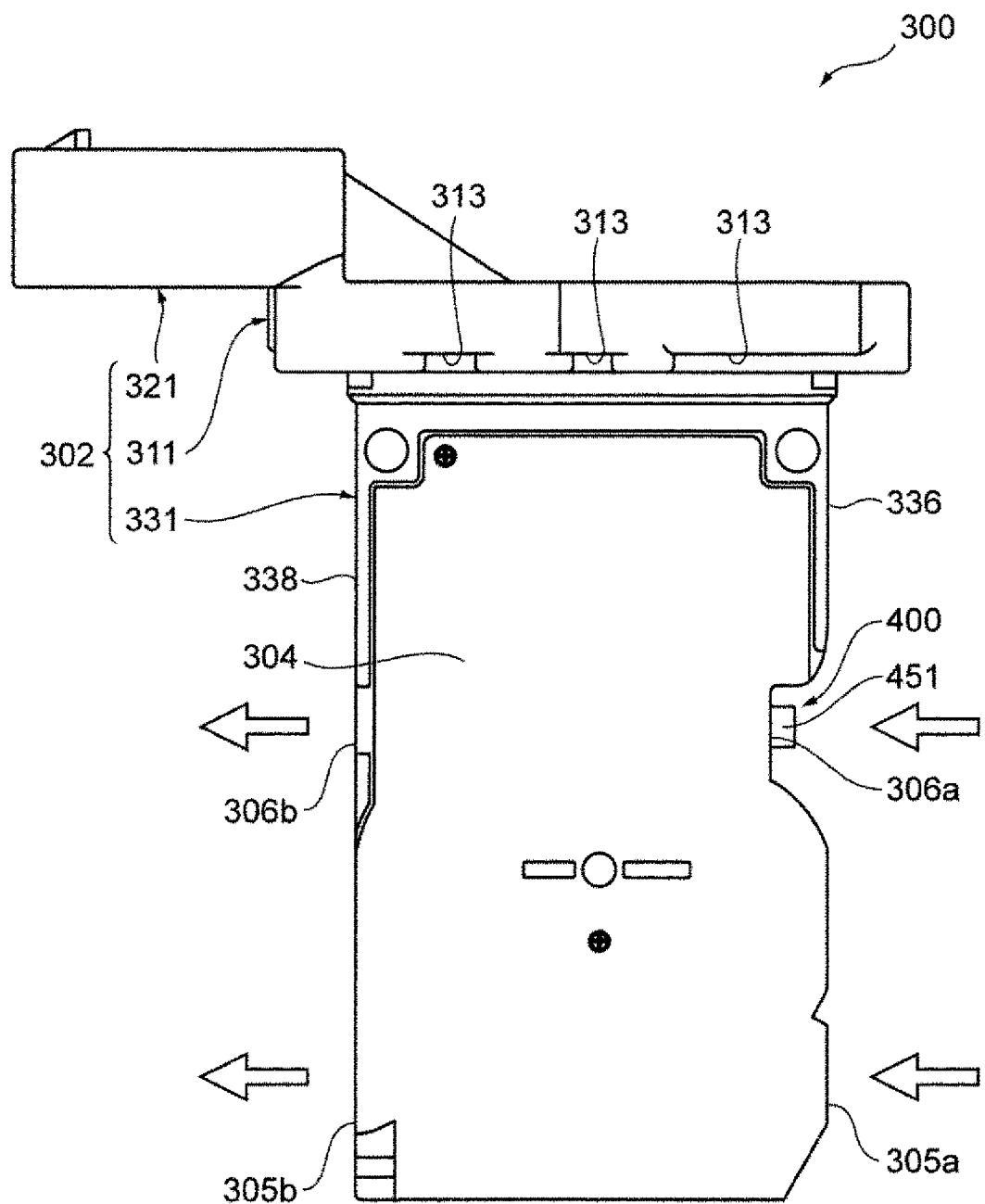
FIG. 2B is a rear view of the physical quantity detection device.
Figure 2C:
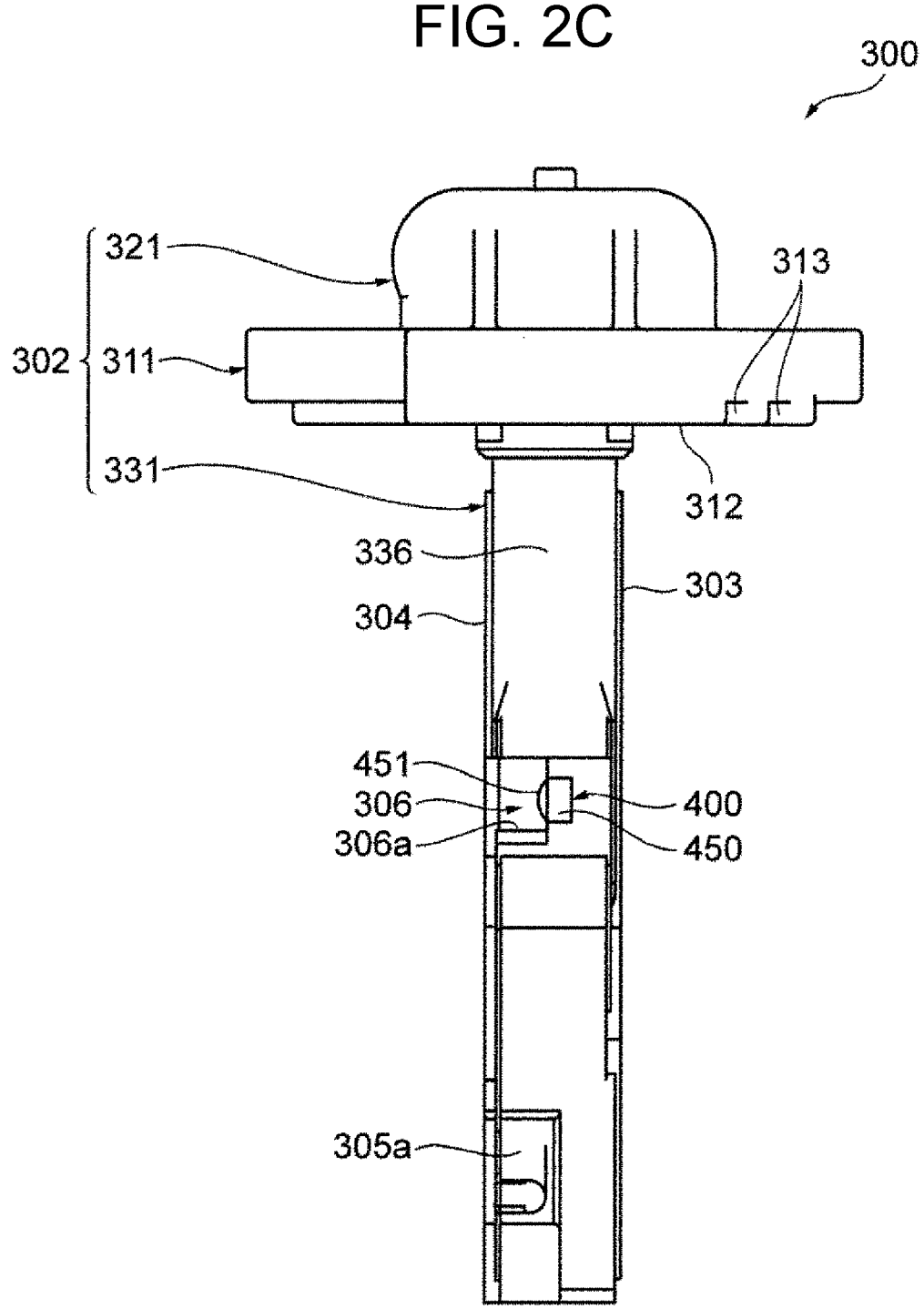
FIG. 2C is a left side view of the physical quantity detection device.
Figure 2D:
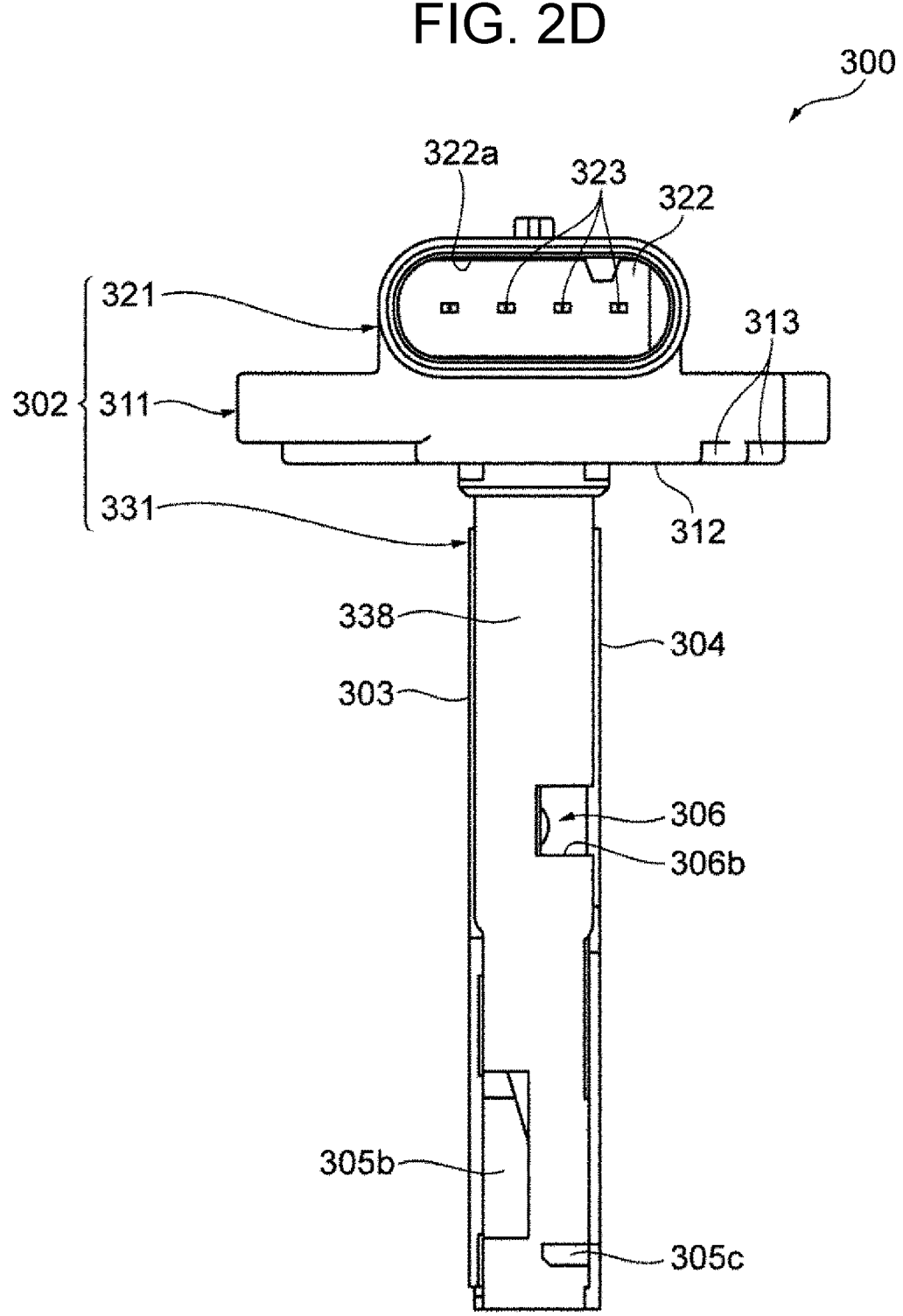
FIG. 2D is a right side view of the physical quantity detection device.
Figure 2E:
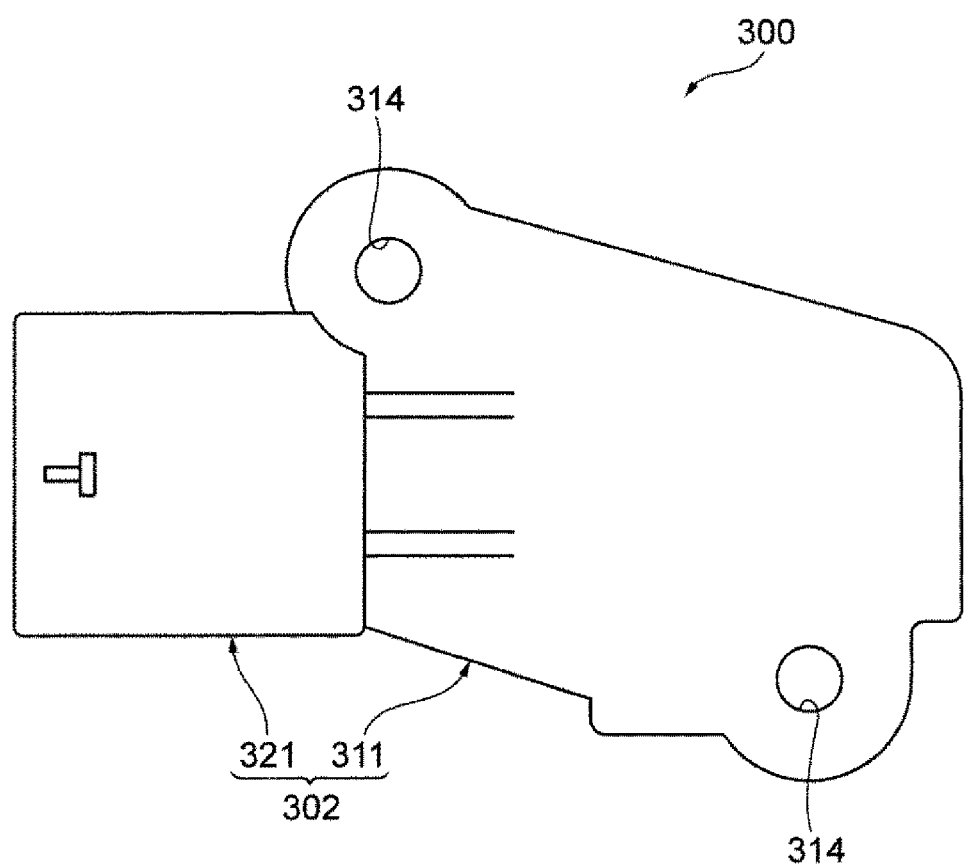
FIG. 2E is a plan view of the physical quantity detection device.
Figure 2F:
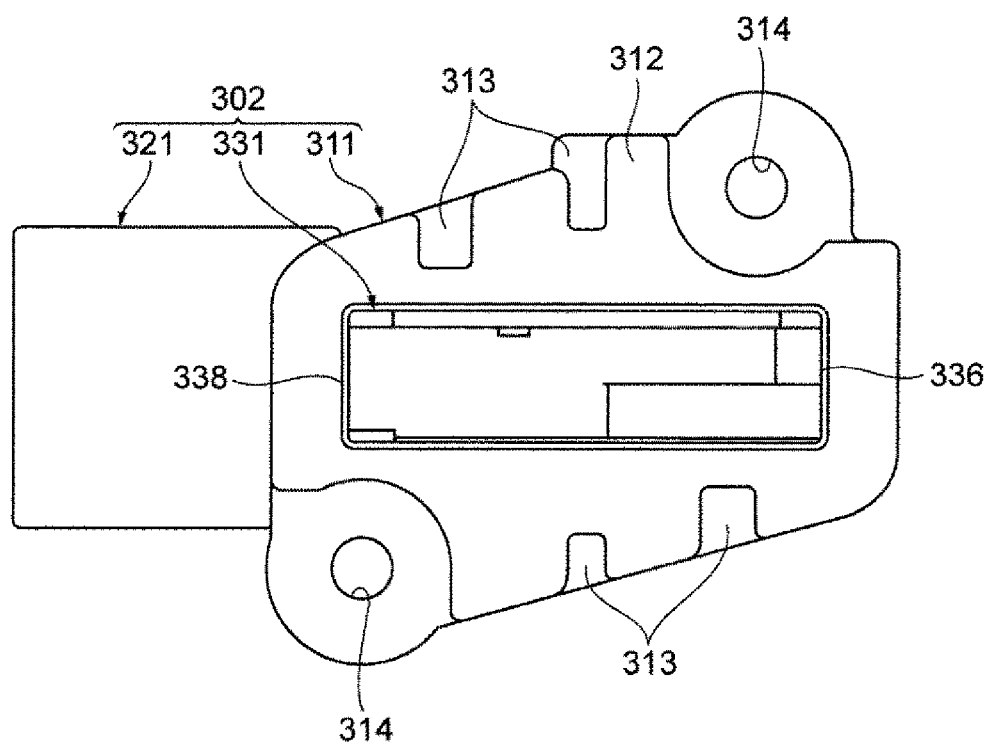
FIG. 2F is a bottom view of the physical quantity detection device.

FIG. 2A to FIG. 2F are views showing the appearance of the physical quantity detection device 300. FIG. 2A is a front view of the physical quantity detection device 300. FIG. 2B is a rear view. FIG. 2C is a left side view. FIG. 2D is a right side view. FIG. 2E is a plan view. FIG. 2F is a bottom view.

The physical quantity detection device 300 includes a housing 302, a front cover 303, and a back cover 304. The housing 302 is formed by molding a synthetic resin material, and includes a flange 311 for fixing the physical quantity detection device 300 to the intake body which is the main passage 124, an external connection unit 321 projecting from the flange 311 and having a connector for electrical connection with external devices, and a measurement unit 331 extending from the flange 311 so as to protrude toward the center of the main passage 124.

Figure 3A:
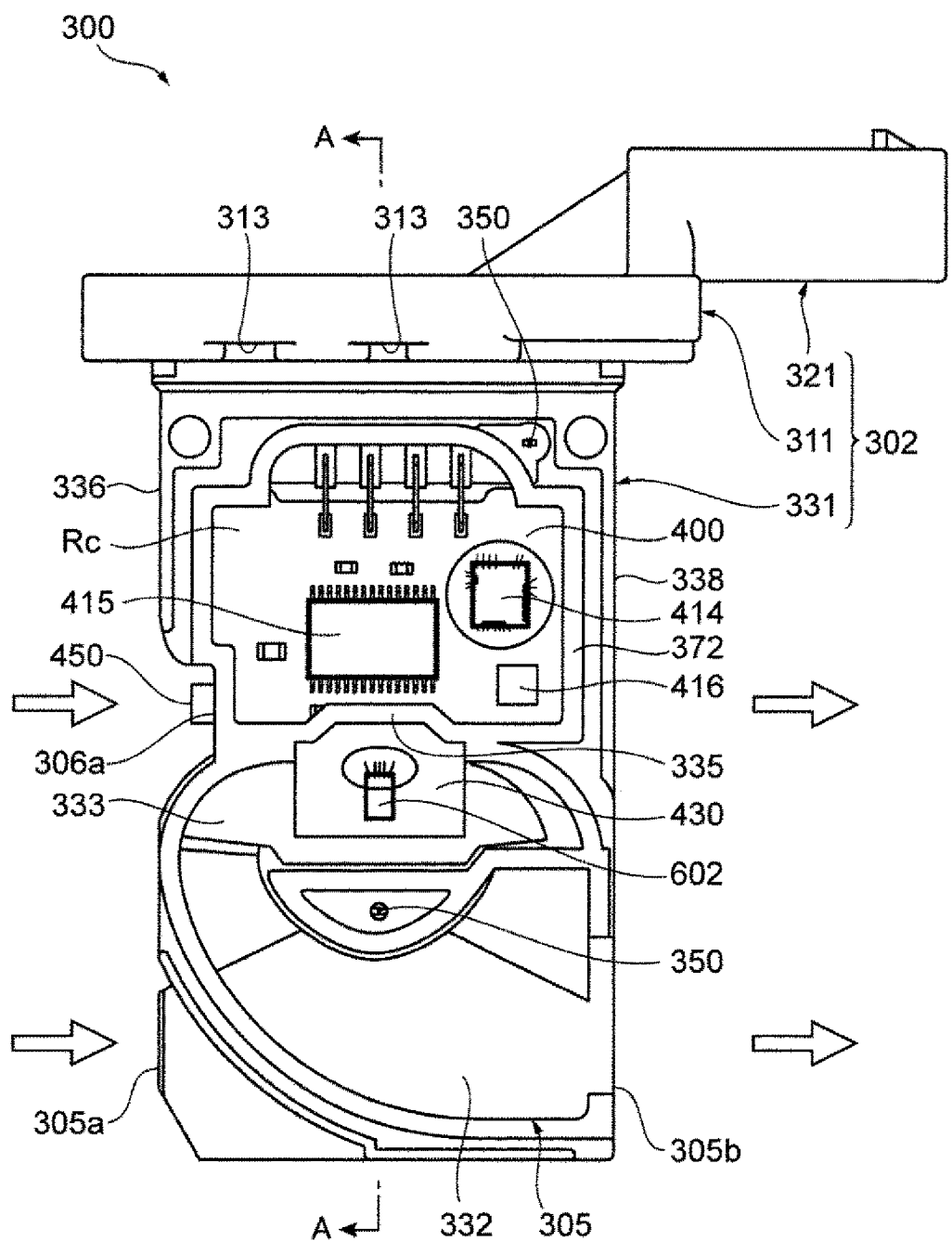
FIG. 3A is a front view showing a state in which the front cover is removed from the physical quantity detection device.
Figure 3B:
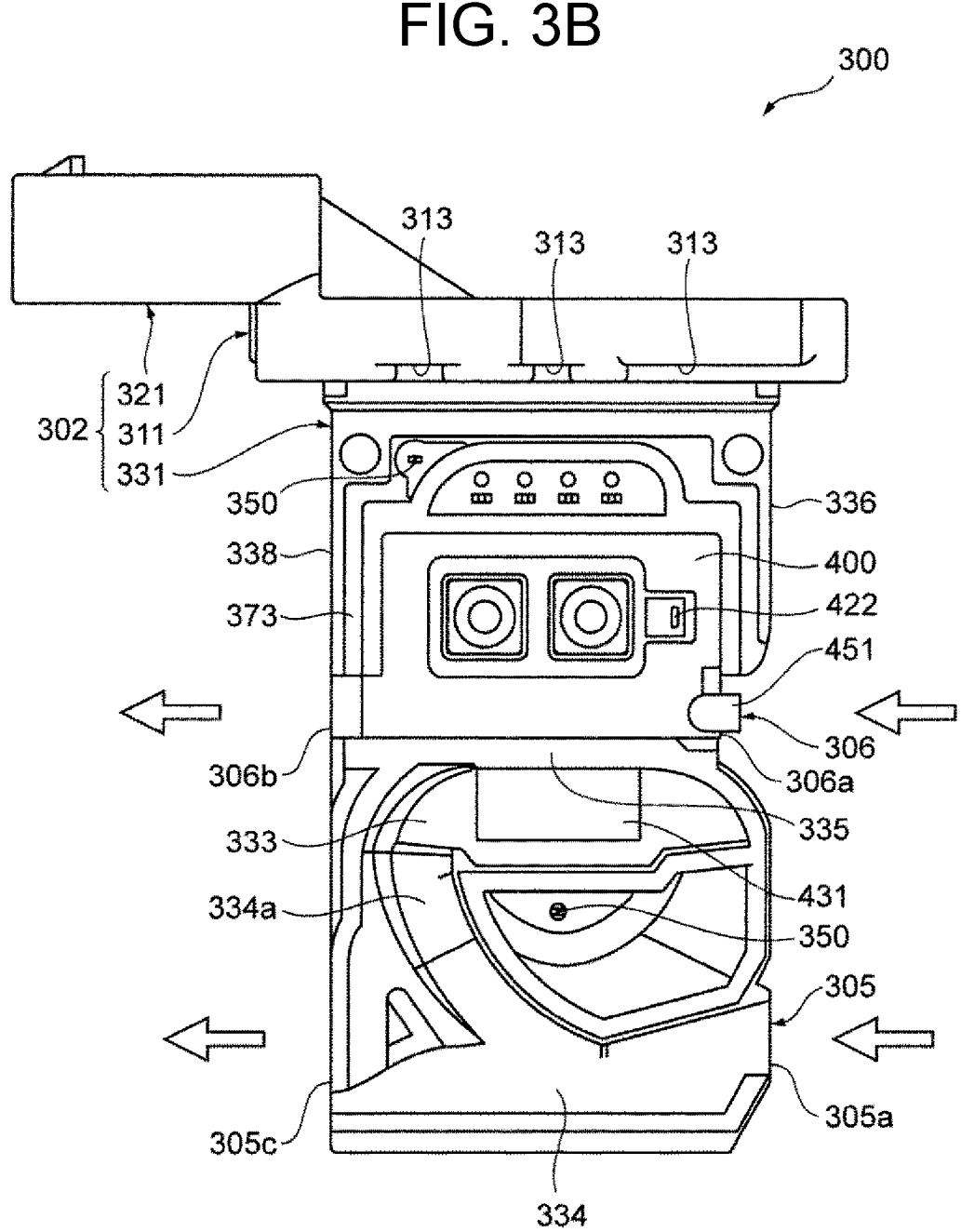
FIG. 3B is a rear view showing a state in which the back cover is removed from the physical quantity detection device.

In the measurement unit 331, a circuit board 400 is integrally provided by insert molding when the housing 302 is molded (see FIG. 3A, FIG. 3B). The circuit board 400 is provided with at least one detection unit for detecting the physical quantity of the measurement target gas 30 flowing through the main passage 124 and a circuit unit for processing the signal detected by the detection unit. The detection unit is placed at a position exposed to the measurement target gas 30 and the circuit unit is placed in the circuit chamber sealed by the front cover 303.

A sub-passage groove is provided on the front and back surfaces of the measurement unit 331, and a first sub-passage 305 is formed in cooperation with the front cover 303 and the back cover 304. A first sub-passage entrance 305a for taking a part of measurement target gas 30 such as intake air into first sub-passage 305 and a first sub-passage exit 305b for returning the measurement target gas 30 from the first sub-passage 305 to the main passage 124 are formed at the distal end portion of the measurement unit 331. A part of the circuit board 400 protrudes in the middle of passage of the first sub-passage 305. A flow rate detection unit 602 (see FIG. 3A) which is a detection unit is arranged in the protruding portion, and the flow rate of the measurement target gas 30 is detected by the flow rate detection unit 602.

A second sub-passage 306 for introducing a part of the measurement target gas 30 such as intake air into a sensor chamber Rs is provided in the middle part of the measurement unit 331 closer to the flange 311 than the first sub-passage 305. The second sub-passage 306 is formed by cooperation of the measurement unit 331 and the back cover 304. The second sub-passage 306 includes a second sub-passage entrance 306a formed through the upstream side external wall 336 to capture the measurement target gas 30 and a second sub-passage exit 306b formed through the downstream side external wall 338 to return the measurement target gas 30 from the second sub-passage 306 to the main passage 124. The second sub-passage 306 is in communication with the sensor chamber Rs formed in the back side of the measurement unit 331. In the sensor chamber Rs, a pressure sensor and a temperature and humidity sensor which are detection units provided on the back side of the circuit board 400 are arranged.

2.2 Effects Based on External Appearance Structure of Physical Quantity Detection Device 300

In the physical quantity detection device 300, the second sub-passage entrance 306a is provided in the middle part of the measurement unit 331 extending from the flange 311 toward the center direction of the main passage 124, and the first sub-passage entrance 305a is provided at the distal end portion of the measurement unit 331. Therefore, instead of from the vicinity of the inner wall surface of the main passage 124, the gas from the vicinity of the center part away from the inner wall surface can be captured into in the first sub-passage 305 and the second sub-passage 306. Therefore, the physical quantity detection device 300 can measure the physical quantity of the gas at a portion distant from the inner wall surface of the main passage 124, and can reduce the measurement error of the physical quantity related to the heat and the flow velocity decrease near the inner wall surface.

The measurement unit 331 has a shape elongated along the axis extending from the external wall of the main passage 124 toward the center, but the thickness width is in a narrow shape as shown in FIG. 2C and FIG. 2D. More specifically, the measurement unit 331 of the physical quantity detection device 300 has a shape in which the side face is thin and the front face is substantially rectangular. Accordingly, the physical quantity detection device 300 can have the first sub-passage 305 of which length is sufficient, and the fluid resistance for the measurement target gas 30 can be suppressed to a small value. Therefore, the physical quantity detection device 300 can suppress the fluid resistance to a small value and measure the flow rate of the measurement target gas 30 with high accuracy.

2.3 Structure and Effect of Flange 311

In the flange 311, multiple dents 313 are provided on the lower surface 312 opposed to the main passage 124 to reduce the heat transfer surface with the main passage 124, so that the physical quantity detection device 300 is less affected by heat. In the physical quantity detection device 300, the measurement unit 331 is inserted into the mounting hole provided in the main passage 124, and the lower surface 312 of the flange 311 is opposed to the main passage 124. The main passage 124 is, for example, an intake body, and the main passage 124 is often maintained at a high temperature. Conversely, when starting up in cold climate, it is conceivable that the main passage 124 is at an extremely low temperature. If such a high temperature or low temperature state of the main passage 124 affects the measurements of various physical quantities, the measurement precision will be lowered. The flange 311 has the dents 313 in the lower surface 312, and a space is formed between the lower surface 312 opposed to the main passage 124 and the main passage 124. Therefore, it is possible to reduce the heat transfer from the main passage 124 to the physical quantity detection device 300, and to prevent deterioration of measurement accuracy due to the heat.

A screw hole 314 of the flange 311 is for fixing the physical quantity detection device 300 to the main passage 124, and a space is formed between the main passage 124 and the surface opposite the main passage 124 around each screw hole 314, so that the surface opposing the main passage 124 around the screw hole 314 is away from the main passage 124. In this configuration, the heat transfer from the main passage 124 to the physical quantity detection device 300 is reduced, and the structure is such that it is possible to prevent the deterioration of measurement accuracy due to heat.

2.4 Structure of External Connection Unit 321

The external connection unit 321 has a connector 322 provided on the upper surface of the flange 311 and protruding from the flange 311 toward the flow-direction downstream side of the measurement target gas 30. The connector 322 is provided with an insertion hole 322a for inserting communication cables for connecting with the control device 200. As shown in FIG. 2D, inside the insertion hole 322a, four external terminals 323 are provided. The external terminal 323 is a terminal for outputting physical quantity information which is the measurement result of the physical quantity detection device 300 and power supply terminals for supplying DC power for the operation of the physical quantity detection device 300.

The connector 322 protrudes from the flange 311 toward the flow-direction downstream side of the measurement target gas 30 and has a shape to be inserted from the flow-direction downstream side toward the upstream side. However, the connector 322 is limited to this shape. For example, the connector 322 may have a shape protruding perpendicularly from the upper surface of the flange 311 to be inserted along the extension direction of the measurement unit 331, and various modifications are possible.

3. Entire Structure of Housing 302 and Effects Thereof 3.1 Structure of Housing

Figure 3D:
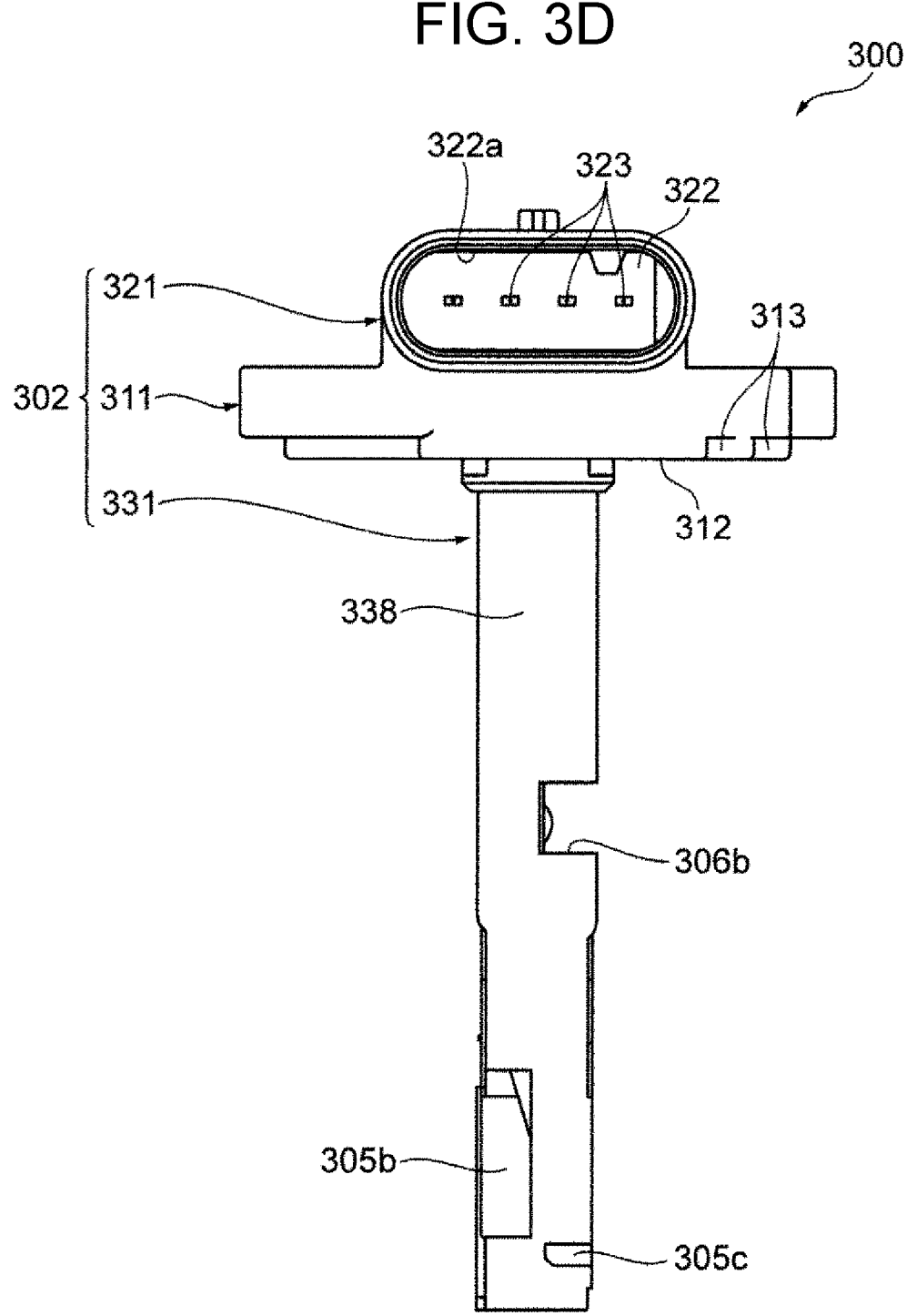
FIG. 3D is a right side view showing a state in which the front cover and the back cover are removed from the physical quantity detection device.
Figure 3E:
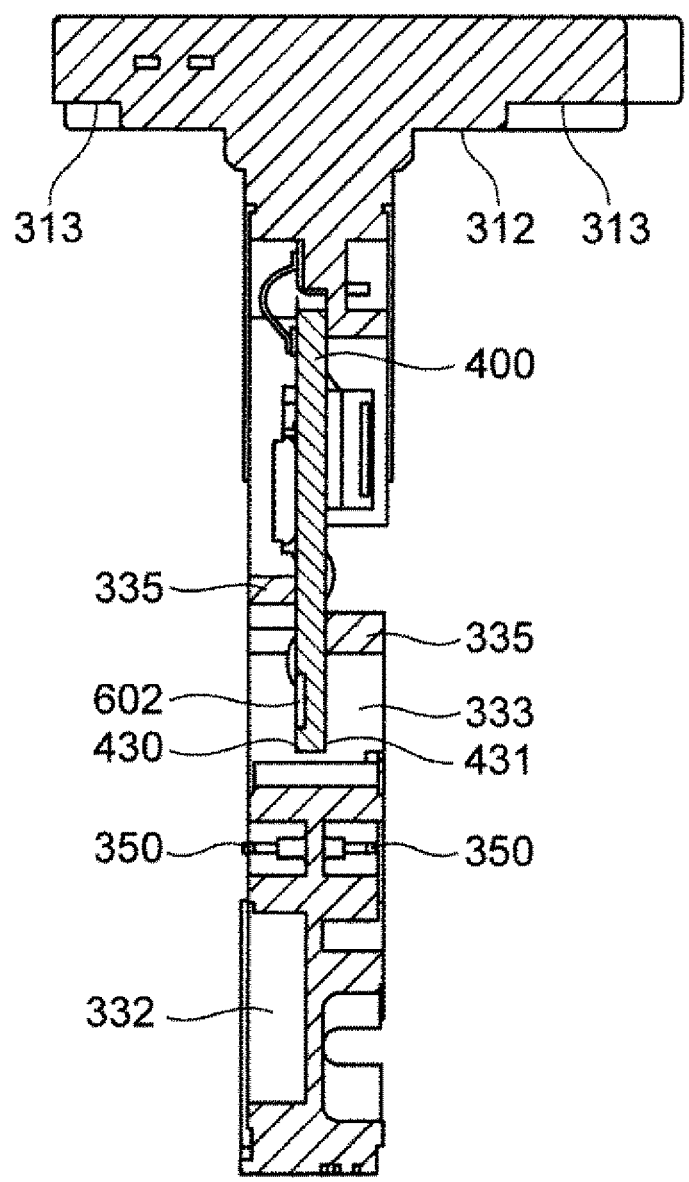
FIG. 3E is a cross-sectional view taken along line A-A of FIG. 3A.

Subsequently, the entire structure of the housing 302 will be described with reference to FIGS. 3A to 3E. FIGS. 3A to 3E are diagrams showing the state of the housing 302 in which the front cover 303 and the back cover 304 are removed from the physical quantity detection device 300. FIG. 3A is a front view of the housing 302. FIG. 3B is a rear view of the housing 302. FIG. 3C is a right side view of the housing 302. FIG. 3D is a left side view of the housing 302. FIG. 3E is a sectional view taken along line A-A of FIG. 3A.

The housing 302 has a structure in which the measurement unit 331 extends from the flange 311 toward the center of the main passage 124. A circuit board 400 is insert molded at the proximal end side of the measurement unit 331. The circuit board 400 is disposed parallel to the surface of the measurement unit 331 at an intermediate position between the front surface and the back surface of the measurement unit 331 and molded integrally with the housing 302, and the base end side of the measurement unit 331 is divided into thickness-direction one side and the other side.

On the front surface side of the measurement unit 331, a circuit chamber Rc for accommodating the circuit unit of the circuit board 400 is formed. On the back surface side of the measurement unit 331, a sensor chamber Rs for accommodating a pressure sensor 421 and a temperature and humidity sensor 422 are formed. The circuit chamber Rc is hermetically sealed by attaching the front cover 303 to the housing 302 and is completely isolated from the outside. On the other hand, by attaching the back cover 304 to the housing 302, the second sub-passage 306 and the sensor chamber Rs which is a space inside the chamber in communication with the external of the measurement unit 331 via the second sub-passage 306 are formed. A part of the circuit board 400 protrudes from a partition wall 335 partitioning the circuit chamber Rc of the measurement unit 331 and the first sub-passage 305 toward the first sub-passage 305, and a flow rate detection unit 602 is provided in the measurement flow path surface 430 of the protruded portion.

3.2 Structure of Sub-Passage Groove

At the length-direction distal end side of the measurement unit 331, a sub-passage groove for forming the first sub-passage 305 is provided. The sub-passage groove for forming the first sub-passage 305 has a front side sub-passage groove 332 shown in FIG. 3A and a back side sub-passage groove 334 shown in FIG. 3B. As shown in FIG. 3A, the front side sub-passage groove 332 gradually bends to the flange 311 which is the proximal end side of the measurement unit 331 as the front side sub-passage groove 332 extends from the first sub-passage exit 305b, which is open through the downstream side external wall 338 of the measurement unit 331, to the upstream side external wall 336. The front side sub-passage groove 332 communicates with an opening unit 333 penetrating the measurement unit 331 in the thickness direction at a position near the upstream side external wall 336. The opening unit 333 is formed along the flow-direction of the measurement target gas 30 of the main passage 124 so as to extend between the upstream side external wall 336 and the downstream side external wall 338.

As shown in FIG. 3B, the backside sub-passage groove 334 moves from the upstream side external wall 336 to the downstream side external wall 338, and is divided into two at the intermediate position between the upstream side external wall 336 and the downstream side external wall 338, and one of them extends in straight line as a discharge passage and opens to an exhaust exit 305c of the downstream side external wall 338, and the other of them gradually bends to the flange 311 which is the proximal end side of the measurement unit 331 as it extends to the downstream side external wall 338, and is in communication with the opening unit 333 in the vicinity of the downstream side external wall 338.

The back side sub-passage groove 334 forms an entrance groove into which the measurement target gas 30 flows from the main passage 124. The front side sub-passage groove 332 forms an exit groove for returning the measurement target gas 30 taken from the back side sub-passage groove 334 to the main passage 124. Since the front side sub-passage groove 332 and the back side sub-passage groove 334 are provided in the distal end portion of the housing 302, a gas in a portion away from the inner wall surface of the main passage 124, i.e., a gas flowing in a portion close to the central portion of the main passage 124, can be captured as the measurement target gas 30. The gas flowing in the vicinity of the inner wall surface of the main passage 124 is affected by the wall surface temperature of the main passage 124 and often has a temperature different from the average temperature of the gas flowing through the main passage 124 such as intake air 20. The gas flowing in the vicinity of the inner wall surface of the main passage 124 often shows a flow velocity lower than the average flow velocity of the gas flowing through the main passage 124. Since the physical quantity detection device 300 according to the embodiment is hardly affected by such an influence, it is possible to suppress a decrease in the measurement accuracy.

As shown in FIG. 3B, a part of the measurement target gas 30 flowing through the main passage 124 is taken into the back side sub-passage groove 334 from the first sub-passage entrance 305a and flows in the back side sub-passage groove 334. A foreign substance having a large mass contained in the measurement target gas 30 flows into the discharge passage extending straight from the branch together with a part of the measurement target gas to be discharged from the exhaust exit 305c of the downstream side external wall 338 to the main passage 124.

The back side sub-passage groove 334 has a shape which becomes deeper as it advances and the measurement target gas 30 gradually moves to the front side of the measurement unit 331 as it flows along the back side sub-passage groove 334. Particularly, the back side sub-passage groove 334 is provided with a sharply inclined portion 334a which is rapidly deepened before the opening unit 333, and a part of the air having a small mass moves along the sharply inclined portion 334a and, in the opening unit 333, the part of the air having a small mass flows at the side of measurement flow path surface 430 of the circuit board 400. On the other hand, a foreign substance having a large mass flows at the side of the measurement flow path surface back surface 431 because it is difficult to change the course suddenly.

As shown in FIG. 3A, the measurement target gas 30 moved to the front side in the opening unit 333 flows along the measurement flow path surface 430 of the circuit board, and heat transfer is performed with the flow rate detection unit 602 provided in the measurement flow path surface 430 so that the flow rate is measured. The air flowing from the opening unit 333 to the front side sub-passage groove 332 flows along the front side sub-passage groove 332 and is discharged to the main passage 124 from the first sub-passage exit 305b that is open to the downstream side external wall 338.

A substance having a large mass such as dust mixed in the measurement target gas 30 has a large inertial force and therefore it is difficult for such a substance having a large mass such as dust mixed in the measurement target gas 30 to suddenly change the course in a deep direction of the groove along the front surface of a portion of the sharply inclined portion 334a where the depth of the groove rapidly increases. For this reason, a foreign substance having a large mass moves toward the measurement flow path surface back surface 431, and it is possible to suppress a foreign substance from passing near the flow rate detection unit 602. In this embodiment, many foreign substances having large masses other than the gas pass through the measurement flow path surface back surface 431 which is the back surface of the measurement flow path surface 430, and therefore, it is possible to reduce the influence of contamination by foreign substances such as oil, carbon, and dust, and to suppress deterioration of measurement accuracy. More specifically, because of a shape that rapidly changes the course of the measurement target gas 30 along an axis transverse to the axis of the flow of the main passage 124, the influence of foreign substances entering the measurement target gas 30 can be reduced.

3.3 Structure and Effects of Second Sub-Passage and Sensor Chamber

The second sub-passage 306 is formed in a straight line extending between the second sub-passage entrance 306a and the second sub-passage exit 306b in parallel with the flange 311 along the flow-direction of the measurement target gas 30. The second sub-passage entrance 306a is formed by cutting out a part of the upstream side external wall 336. The second sub-passage exit 306b is formed by cutting out a part of the downstream side external wall 338. More specifically, as shown in FIG. 3C, at a position continuously along the upper surface of partition wall 335, the second sub-passage entrance 306a and the second sub-passage exit 306b are formed by cutting out a portion of the upstream side external wall 336 and a portion of the downstream side external wall 338 from the back surface side of measurement unit 331. The second sub-passage entrance 306a and the second sub-passage exit 306b are cut out to a depth position which is the same as the back surface and surface of the circuit board 400. The second sub-passage 306 functions as a cooling channel for cooling a board main body 401 as the measurement target gas 30 passes along the back surface of the board main body 401 of the circuit board 400. The circuit board 400 tends to have heat of an LSI and a microcomputer. The heat can be transferred to the back surface of the board main body 401 and dissipated by the measurement target gas 30 passing through the second sub-passage 306.

The sensor chamber Rs is provided at the proximal end side of the measurement unit 331 with respect to the second sub-passage 306. A part of the measurement target gas 30 flowing from the second sub-passage entrance 306a into the second sub-passage 306 flows into the sensor chamber Rs, and the temperature and humidity sensor 422 and the pressure sensor 421 in the sensor chamber Rs detect the relative humidity and the pressure, respectively. Since the sensor chamber Rs is located at the proximal end side of the measurement unit 331 with respect to the second sub-passage 306, the influence of the dynamic pressure of the measurement target gas 30 passing through the second sub-passage 306 can be reduced. Therefore, the detection accuracy of the pressure sensor 421 in the sensor chamber Rs can be improved.

The sensor chamber Rs is located at the proximal end side of the measurement unit 331 with respect to the second sub-passage 306, and therefore, when the measurement unit 331 is attached to the intake passage with the distal end side facing downward, for example, contaminants and water droplets flowing together with the measurement target gas 30 in the second sub-passage 306 can be prevented from adhering to the pressure sensor 421 and the temperature and humidity sensor 422 disposed upstream thereof.

The pressure sensor 421 and the temperature and humidity sensor 422 are less susceptible to the flow of the measurement target gas 30 compared to the flow rate detection unit 602, and can be provided in the sensor chamber Rs adjacent to the second sub-passage 306 in a straight line. On the other hand, the flow rate detection unit 602 requires a certain flow rate or more, it is necessary to keep dust and contaminants away, and the influence on pulsation also needs to be considered. Therefore, the flow rate detection unit 602 is provided in the first sub-passage 305 having a loop shape.

Figure 4A:
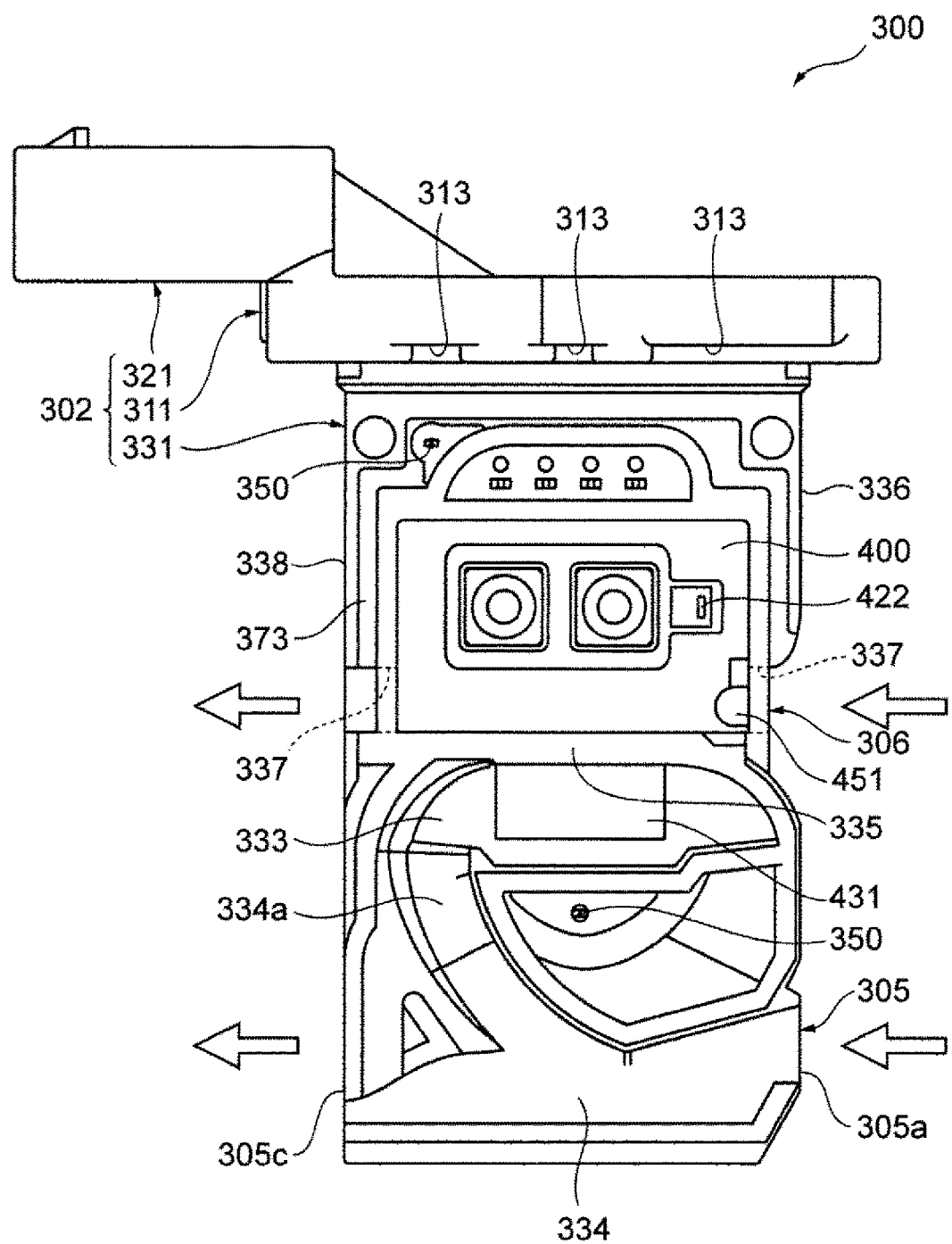
FIG. 4A is a rear view illustrating another embodiment of the housing.

FIG. 4A and FIG. 4B are diagrams showing another mode of second sub-passage.

In this mode, instead of cutting out the upstream side external wall 336 and the downstream side external wall 338, a through hole 337 is provided in the upstream side external wall 336 and the downstream side external wall 338 to form the second sub-passage entrance 306a and the second sub-passage exit 306b. Like the second sub-passage shown in FIG. 3B to FIG. 3E, when the upstream side external wall 336 and the downstream side external wall 338 are respectively cut out to form the second sub-passage entrance 306a and the second sub-passage exit 306b, the width of the upstream side external wall 336 and the width of the downstream side external wall 338 are locally narrowed at such a position, so that the measurement unit 331 may be deformed in an almost angle shape from the notch being a starting point due to heat shrinkage or the like during molding. According to this mode, since the through hole is provided instead of the notch, it is possible to prevent the measurement unit 331 from being bent in a substantially square shape. Therefore, it is possible to prevent the position and direction of the detection unit with respect to the measurement target gas 30 from changing due to distortion in the housing 302, thereby preventing the detection accuracy from being affected, and constant detection accuracy can always be secured without individual differences.

In the back cover 304, a partition wall partitioning between the second sub-passage 306 and the sensor chamber Rs may be provided. According to such a configuration, it is possible to indirectly cause the measurement target gas 30 to flow from the second sub-passage 306 to the sensor chamber Rs, to reduce the influence of the dynamic pressure on the pressure sensor, and to suppress contaminants and water droplets adhered to the temperature and humidity sensor 3.4 Shape and Effect of Front Cover 303 and Back Cover 304

Figure 5A:
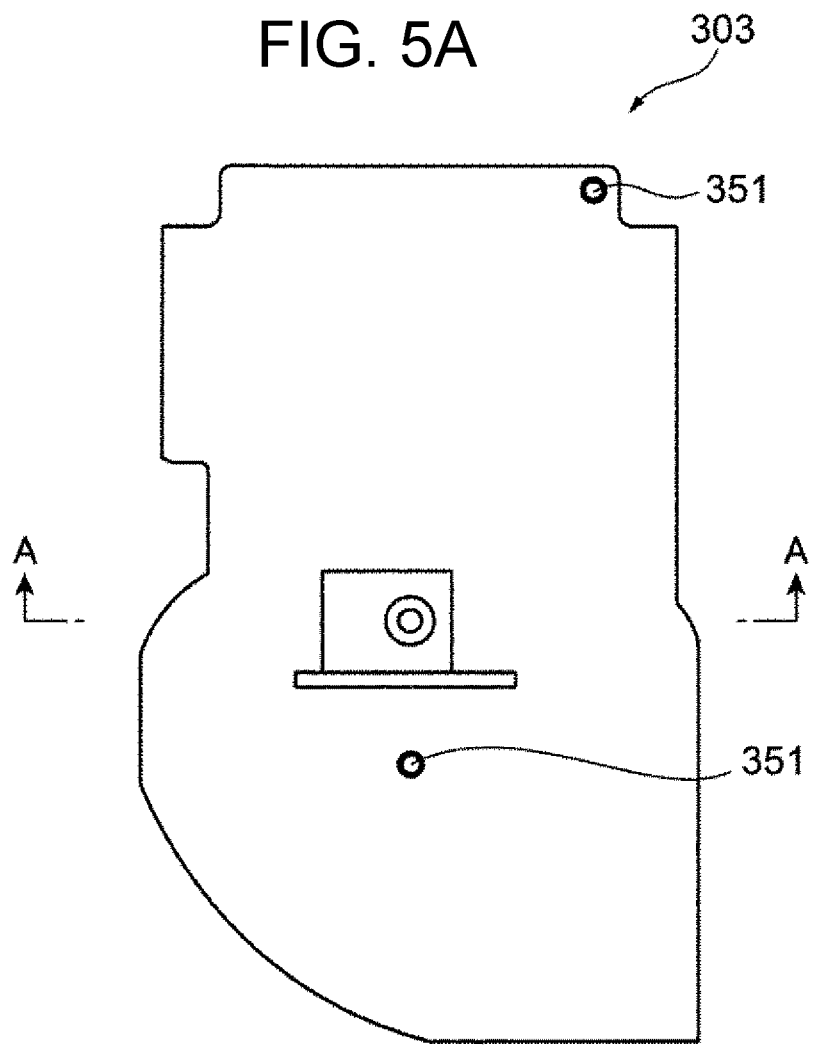
FIGS. 5A and 5B are views for explaining the structure of the front cover.
Figure 5B:
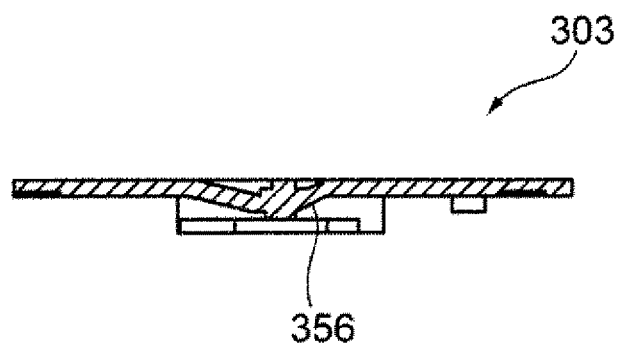
Figure 6A:
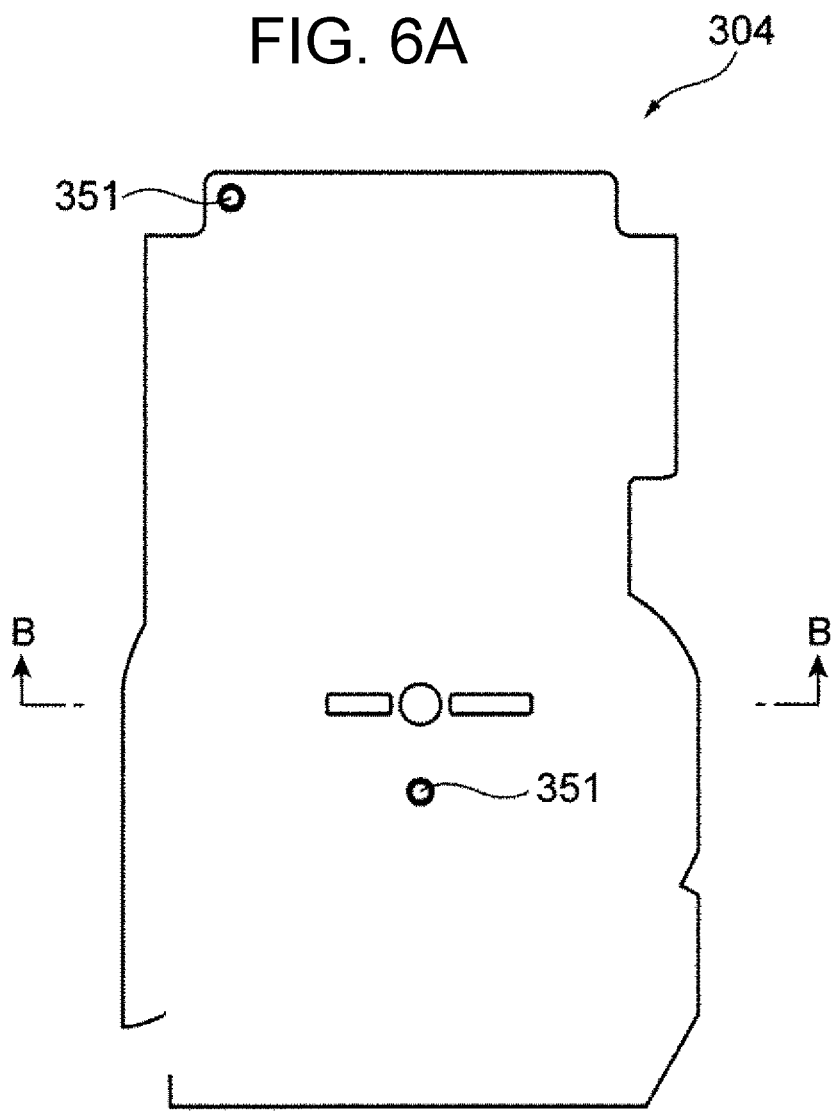
FIGS. 6A and 6B are views for explaining the configuration of the rear cover.
Figure 6B:
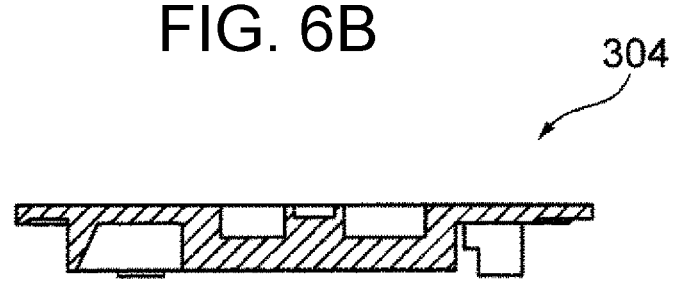

FIGS. 5A and 5B are figures showing an appearance of the front cover 303. FIG. 5A is a front view. FIG. 5B is a B-B line sectional view of FIG. 5A. FIGS. 6A and 6B show the appearance of the back cover 304. FIG. 6A is a front view, and FIG. 6B is a B-B cross sectional view of FIG. 6A.

In FIGS. 5A-5B and FIGS. 6A-6B, the front cover 303 and the back cover 304 close the front side sub-passage groove 332 and the back side sub-passage 334 of the housing 302, thereby forming a first sub-passage 305. In addition, the front cover 303 makes the hermetically sealed circuit chamber Rc, and the back cover 304 closes the recess of the back surface side of the measurement unit 331 to make the second sub-passage 306 and the sensor chamber Rs communicating with the second sub-passage 306.

The front cover 303 has a protrusion unit 356 at a position facing the flow rate detection unit 602 and is used to form a stop between the flow rate detection unit 602 and the measurement flow path surface 430. Therefore, it is desirable that molding accuracy is high. Since the front cover 303 and the back cover 304 are made by a resin molding process for injecting a thermoplastic resin into a mold, the front cover 303 and the back cover 304 can be made with high molding precision.

The front cover 303 and the back cover 304 are provided with multiple fixing holes 351 into which multiple fixation pins 350 protruding from the measurement unit 331 are inserted. The front cover 303 and the back cover 304 are respectively attached to the front surface and the back surface of the measurement unit 331, and at this time, the fixing pin 350 is inserted into the fixing hole 351 and positioned. Then, bonding is performed by laser welding or the like along the edges of the front side sub-passage groove 332 and the back side sub-passage groove 334, and likewise bonding is performed by laser welding or the like along edges of the circuit chamber Rc and the sensor chamber Rs.

3.5 Fixing Structure and Effects of Circuit Board 400 by Housing 302

Next, fixing of the circuit board 400 to the housing 302 by the resin molding process will be described. The circuit board 400 is molded integrally with the housing 302 so that the flow rate detection unit 602 of the circuit board 400 is arranged in the predetermined place of the sub-passage groove forming the sub-passage, for example, in the present embodiment, the opening unit 333 which is the connection part between the front side sub-passage groove 332 and the back side sub-passage groove 334.

In the measurement unit 331 of the housing 302, parts for fixing the outer peripheral edge portion of the base unit 402 of the circuit board 400 by resin molding on the housing 302 are provided as fixing units 372 and 373. The fixing units 372 and 373 fix the outer peripheral edge portions of the base unit 402 of the circuit board 400 by sandwiching them from the front side and the back side.

The housing 302 is manufactured by a resin molding process. In this resin molding process, the circuit board 400 is built in the resin of the housing 302 and fixed in the housing 302 by resin molding. Accordingly, the shape of the circuit board 400 of the sub flow passage for flow rate detection unit 602 to measure the flow rate by performing heat transfer with measurement target gas 30, such as front side sub-passage groove 332 and back side sub-passage groove 334, can be maintained with extremely high accuracy, and it is possible to suppress errors and variations occurring in each circuit board 400 to very small values. As a result, the measurement accuracy of the circuit board 400 can be greatly improved. For example, the measurement accuracy can be dramatically improved as compared with a method of fixing using a conventional adhesive.

The physical quantity detection device 300 is produced by mass production in many cases, and there is a limitation on the improvement of measurement accuracy in the method of adhesion with an adhesive while strictly performing measuring here. However, as in the present embodiment, the circuit board 400 is fixed at the same time as forming the sub-passage in the resin molding step for molding the sub-passage through which the measurement target gas 30 flows, so that the variation in the measurement accuracy can be greatly reduced, and it is possible to greatly improve the measurement accuracy of the physical quantity detection device 300.

For example, this will be further explained with the embodiment shown in FIG. 3A to FIG. 3E. The circuit board 400 can be fixed to the housing 302 with high accuracy so that the relationship between the front side sub-passage groove 332, the back side sub-passage groove 334, and the flow rate detection unit 602 has a prescribed relationship. In this way, in the mass-produced physical quantity detection device 300, the positional relationships between the flow rate detection unit 602 of each circuit board 400 and the first sub-passage 305 and the shapes thereof and the like can be obtained regularly and constantly with an extremely high accuracy.

With the first sub-passage 305 in which the flow rate detection unit 602 of the circuit board 400 is fixedly arranged, for example, the front side sub-passage groove 332 and the back side sub-passage groove 334 can be molded with extremely high precision, so that the operation of forming the first sub-passage 305 from these sub-passage grooves 332 and 334 is a work of covering both surfaces of the housing 302 with the front cover 303 and the back cover 304. This work is very simple, and it is a work process involving few factors to lower the measurement accuracy. In addition, the front cover 303 and the back cover 304 are produced by process with resin molding with a high forming accuracy. Accordingly, it is possible to complete the sub-passage provided in a prescribed relationship with the flow rate detection unit 602 of the circuit board 400 with high accuracy. According to such a method, in addition to the improvement of the measurement accuracy, high productivity can be obtained.

In contrast to this, a thermal flow rate meter was manufactured by manufacturing a sub-passage and then attaching a measurement unit to the sub-passage with an adhesive. In the method of using the adhesive as described above, the thickness variation of the adhesive is large, and the bonding position and the bonding angle vary from product to product. Therefore, there was a limitation on the increase of the measurement accuracy. Furthermore, when these tasks are performed in a mass production process, it is extremely difficult to improve the measurement accuracy.

In the embodiment according to the present invention, the sub-passage groove for molding the first sub-passage 305 with a resin mold is formed at the same time as fixing the circuit board 400 by resin molding. Therefore, the flow rate detection unit 602 can be fixed to the shape of the sub-passage groove and the sub-passage groove with an extremely high accuracy.

The parts related to the flow rate measurement, for example, the flow rate detection unit 602 and the measurement flow path surface 430 to which the flow rate detection unit 602 is attached, are provided on the front surface of the circuit board 400. The flow rate detection unit 602 and the measurement flow path surface 430 are exposed from the resin molding the housing 302. More specifically, the flow rate detection unit 602 and the measurement flow path surface 430 are not covered with the resin molding the housing 302. The flow rate detection unit 602 of the circuit board 400 and the measurement flow path surface 430 are used as they are even after resin molding of the housing 302 and used for the flow rate measurement of the physical quantity detection device 300. As a result, the measurement accuracy improves.

In the embodiment according to the present invention, the circuit board 400 is fixed to the housing 302 having the first sub-passage 305 by integrally molding the circuit board 400 with the housing 302, the circuit board 400 can be reliably fixed to the housing 302. In particular, since the protrusion unit 403 of the circuit board 400 protrudes into the first sub-passage 305 through the partition wall 335, the sealing property between the first sub-passage 305 and the circuit chamber Rc is high, and it is possible to prevent the measurement target gas 30 from leaking from the first sub-passage 305 to the circuit chamber Rc and to prevent the circuit component, the wiring, and the like of the circuit board 400 from coming into contact with the measurement target gas 30 and corroding.

3.6 Structure and Effects of Terminal Connection Unit 320

Figure 9A:
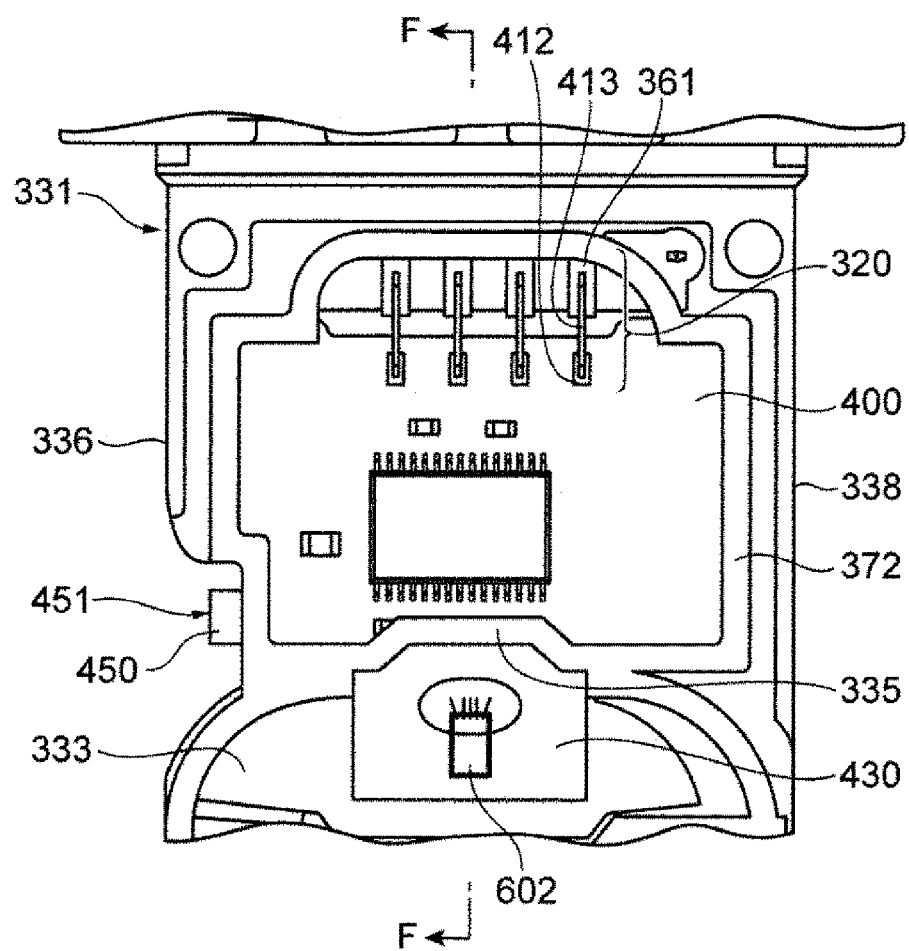
FIG. 9A is a view for explaining the structure of the terminal connecting unit.
Figure 9B:
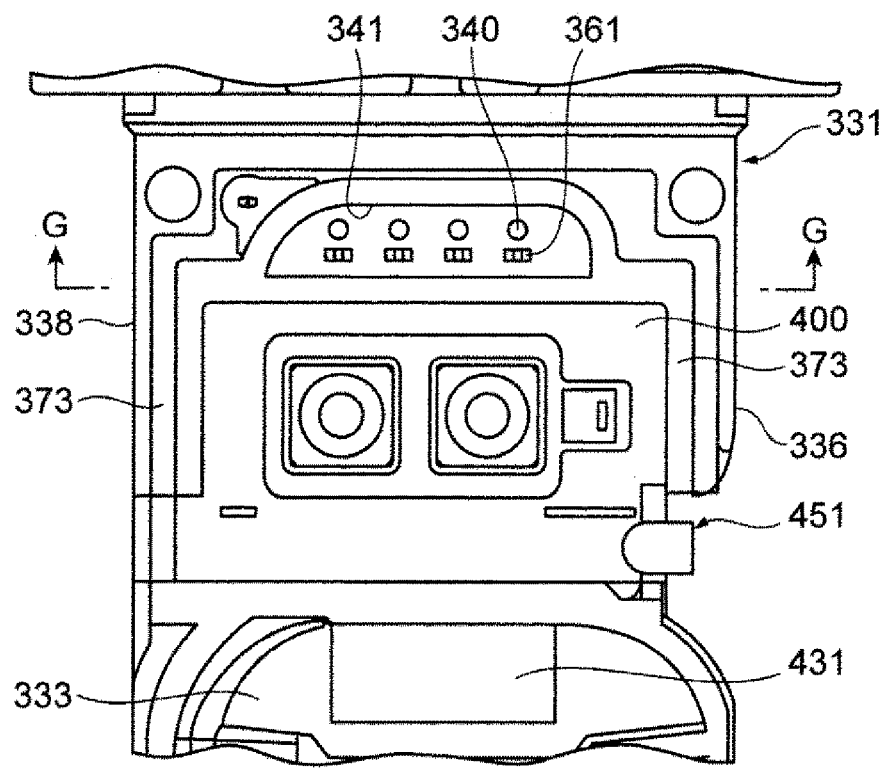
FIG. 9B is a view for explaining the structure of the terminal connecting unit.
Figure 9C:
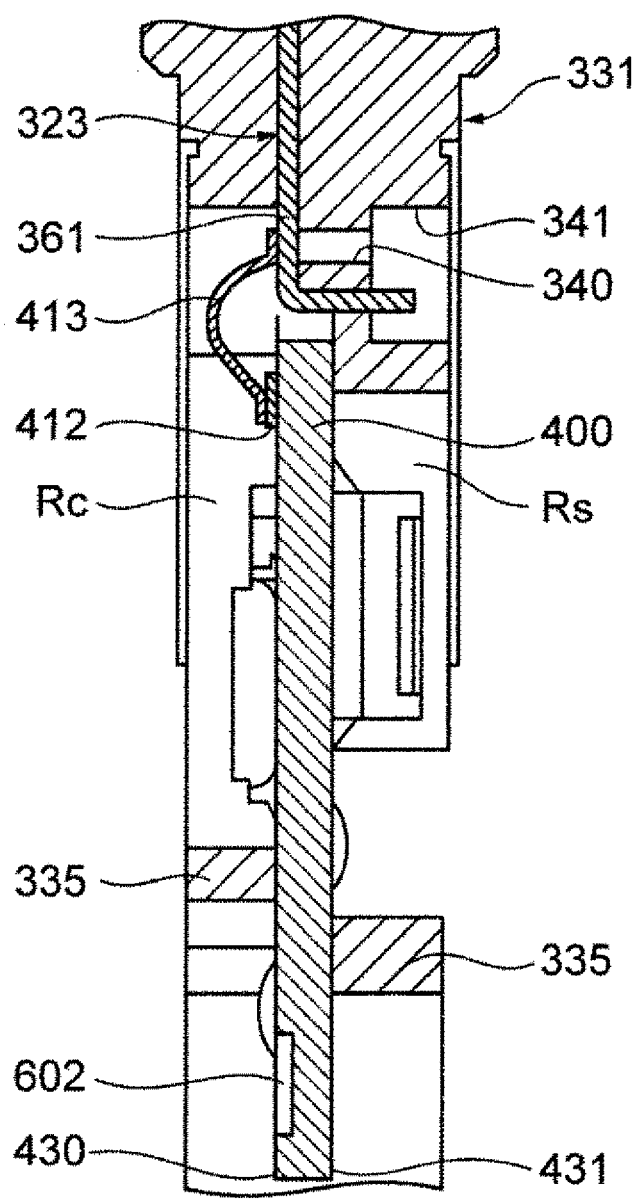
FIG. 9C is a cross-sectional view taken along line F-F of FIG. 9A.
Figure 9D:
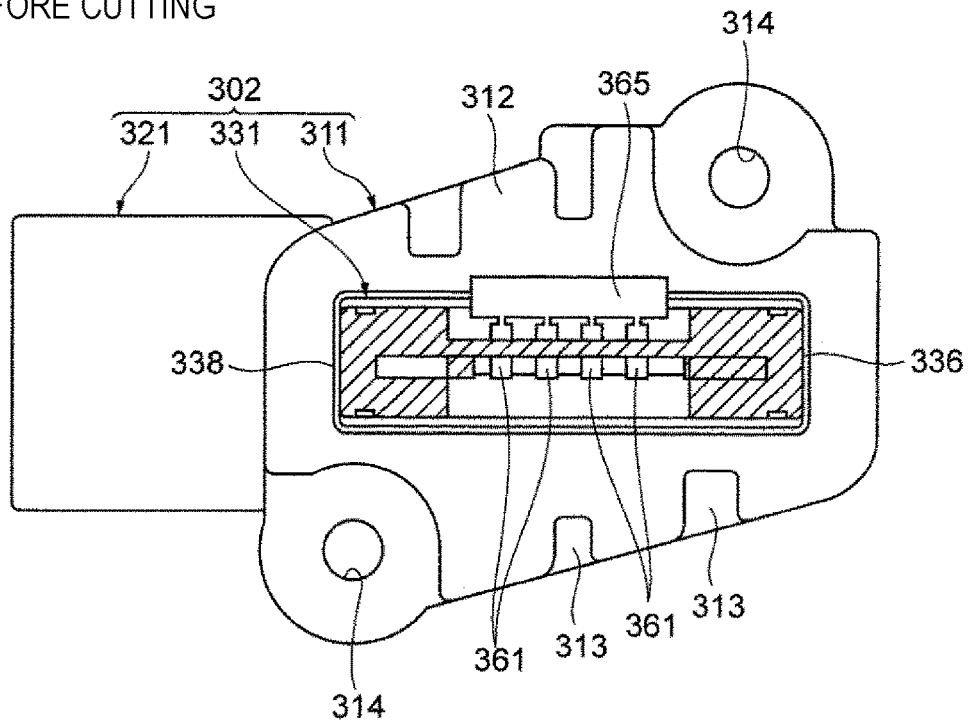
FIGS. 9D and 9E are cross-sectional views taken along line G-G of FIG. 9B.
Figure 9E:
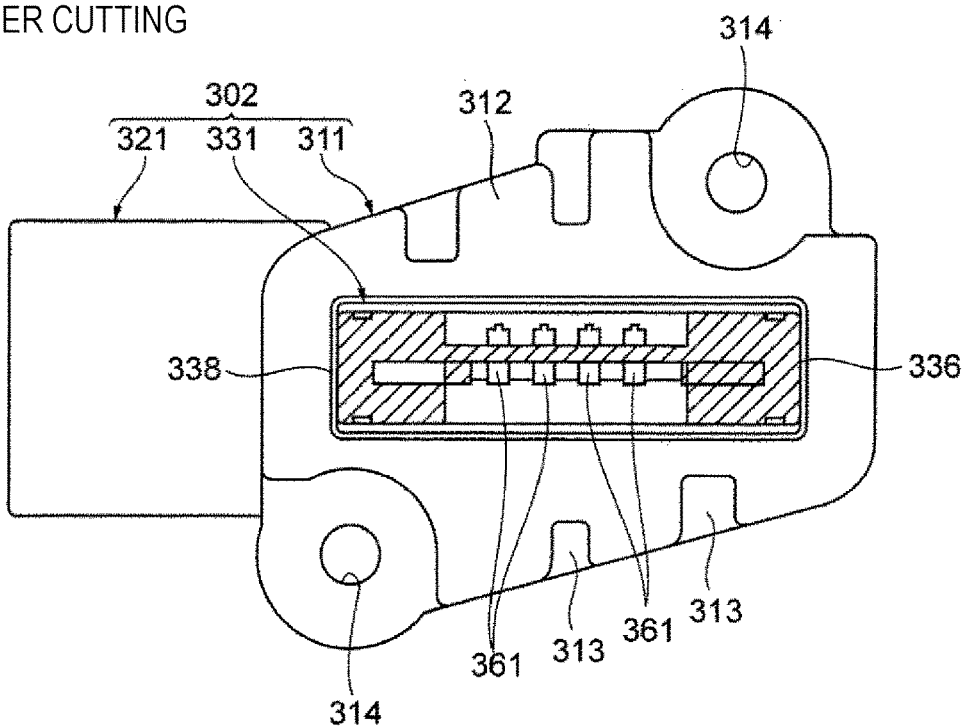

Next, the structure of the terminal connection unit will be described below with reference to FIG. 9A to FIG. 9E. FIG. 9A is a diagram for explaining the structure of the terminal connection unit. FIG. 9B is a diagram for explaining the structure of the terminal connection unit. FIG. 9C is a line F-F sectional view of FIG. 9A. FIGS. 9D and 9E are line G-G sectional views of FIG. 9B.

In the terminal connection unit 320, the inner end unit 361 of the external terminal 323 and the connection terminal 412 of the circuit board 400 are connected by an aluminum wire or a gold wire 413. As shown in FIG. 9A, the inner end unit 361 of each external terminal 323 protrudes from the side of the flange 311 into the circuit chamber Rc and arranged side by side with a predetermined distance from each other according to the position of the connection terminal 412 of the circuit board 400.

As shown in FIG. 9C, the inner end unit 361 is disposed at a position approximately on the surface of the front surface of the circuit board 400. The distal end thereof is bent in a substantially L shape from the front surface to the back surface side of the measurement unit 331 and protrudes to the back surface of the measurement unit 331. As shown in FIG. 9D, a distal end of each inner end unit 361 is connected by a connecting portion 365, and as shown in FIG. 9E, after the molding, the connecting portions 365 are separated and divided individually.

Each inner end unit 361 is fixed to the housing 302 by a resin mold in a molding process so that the inner end unit 361 and the circuit board 400 are arranged on the same plane. Each inner end unit 361 is fixed to the housing 302 by a resin molding process in a state in which they are joined together by the connecting portion 365 so as to prevent deformation and dislocation. After being fixed to the housing 302, the connecting portion 365 is disconnected.

The inner end unit 361 is molded in a state sandwiched between the front surface side and the back surface side of the measurement unit 331. At that time, the front surface of the inner end unit 361 is brought into contact with the mold over the entire surface and the fixing pin is brought into contact with the back surface of the inner end unit 361. Accordingly, the front surface of the inner end unit 361 to which the aluminum wire or the gold wire is welded can be completely exposed without being covered with the mold resin due to resin leakage, and it is easy to weld the gold wire. A pin hole 340 formed by holding the inner end unit 361 with the fixing pin is formed in the measurement unit 331.

The distal end of the inner end unit 361 protrudes into the recessed unit 341 formed in the back surface of the measurement unit 331. The recessed unit 341 is covered with the back cover 304, and the periphery of the recessed unit 341 is joined to the back cover 304 continuously by laser welding or the like to form a hermetically sealed chamber inner space. Therefore, it is possible to prevent the inner end unit 361 from coming into contact with the measurement target gas 30 and corroding.

4. External Appearance of Circuit Board 400

4.1 Formation of Measurement Flow Path Surface 430 Having Flow Rate Detection Unit 602

The appearance of the circuit board 400 is shown in FIG. 7A to FIG. 7F. The hatched portion on the external appearance of the circuit board 400 indicates the fixing surface 432 and the fixing surface 434 which cover and fix the circuit board 400 by the resin when the housing 302 is molded in the resin molding process.

Figure 7A:
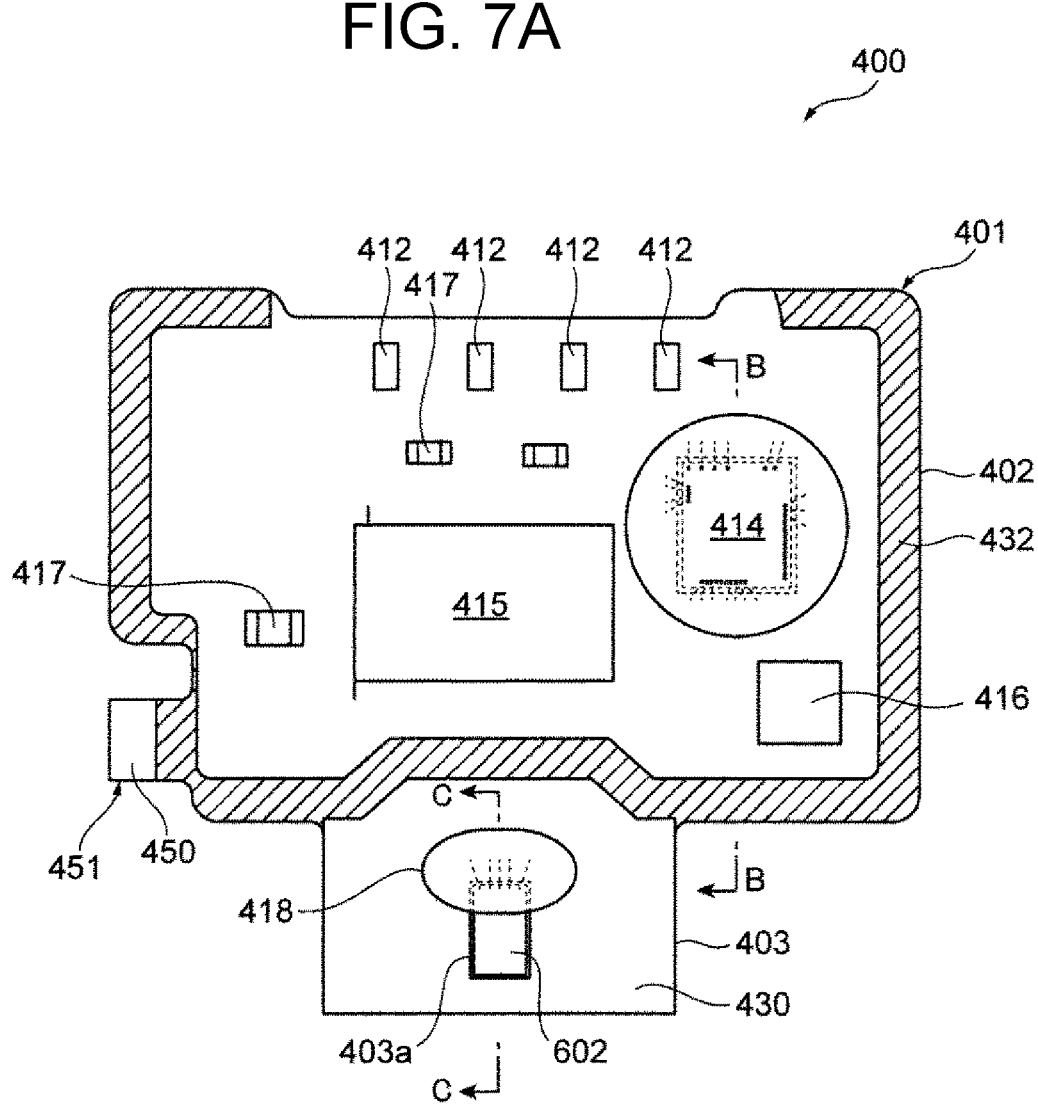
FIG. 7A is a front view of the circuit board.
Figure 7C:
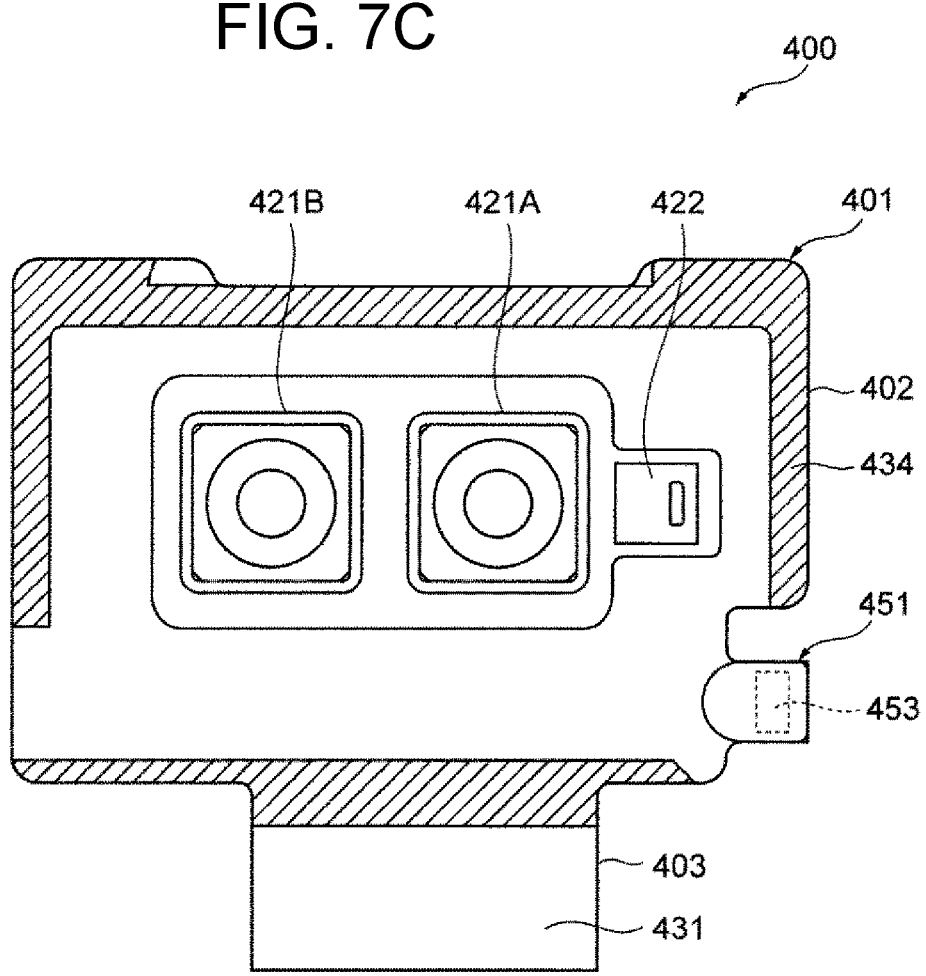
FIG. 7C is a rear view of the circuit board.
Figure 7D:
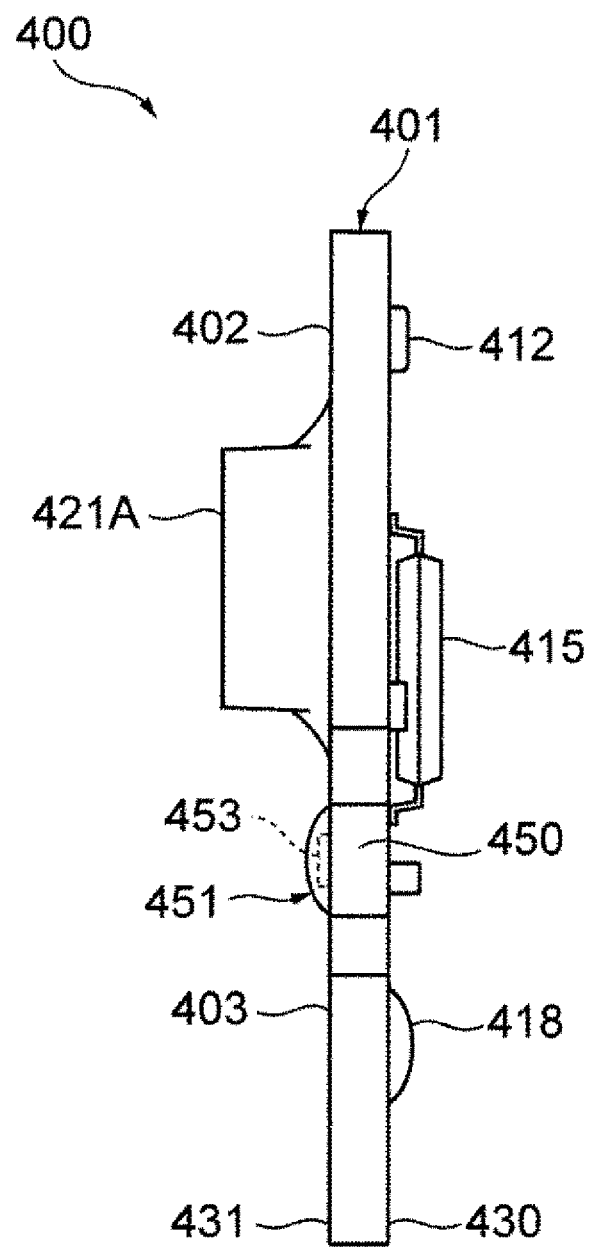
FIG. 7D is a left side view of the circuit board.
Figure 7E:
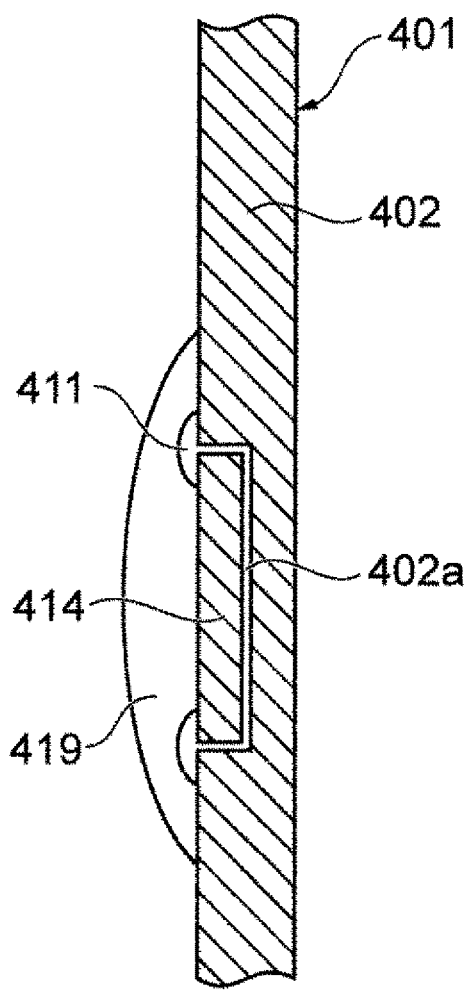
FIG. 7E is a cross-sectional view taken along line B-B of FIG. 7A.
Figure 7F:
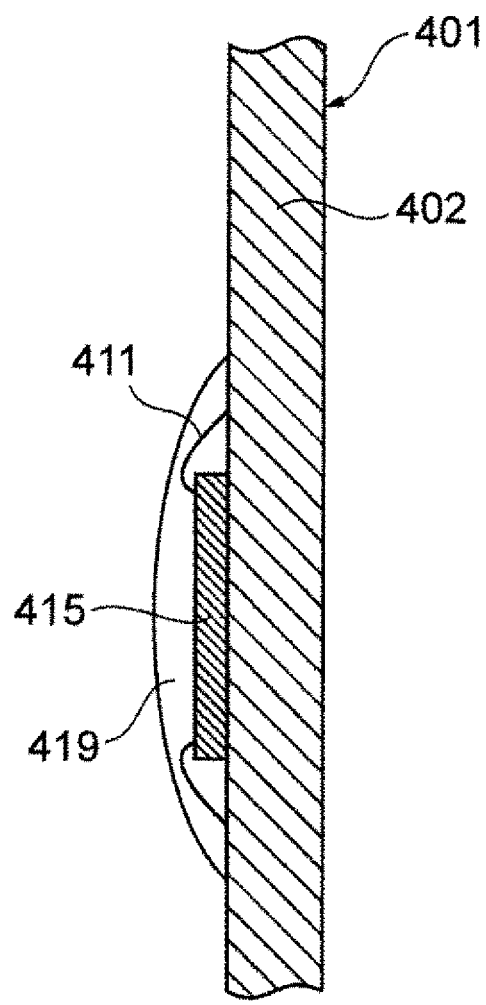
FIG. 7F is a view showing another embodiment corresponding to a cross section taken along line B-B of FIG. 7A.
Figure 7G:
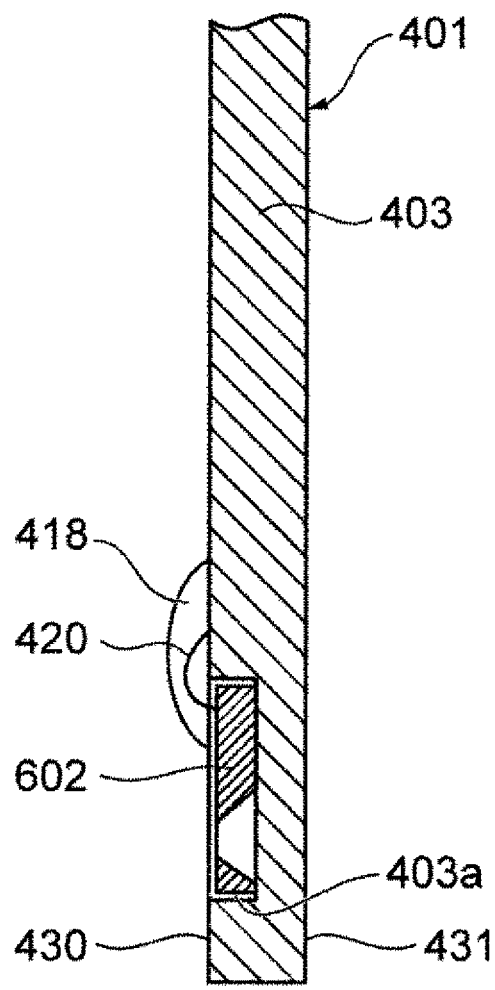
FIG. 7G is a cross-sectional view taken along line C-C of FIG. 7A.

FIG. 7A is a front view of the circuit board. FIG. 7B is a right side surface diagram of the circuit board. FIG. 7C is a back surface diagram of the circuit board. FIG. 7D is a left side surface diagram of the circuit board. FIG. 7E and FIG. 7F are B-B line sectional views showing the cross-section of the LSI portion of FIG. 7A. FIG. 7G is a line C-C sectional view of the detection unit of FIG. 7A.

The circuit board 400 has a board main body 401. The circuit unit and the flow rate detection unit 602 which is a sensing element are provided on the front surface of the board main body 401. The pressure sensor 421 and the temperature and humidity sensor 422 which are sensing elements are provided on the back surface of the board main body 401. The board main body 401 is made of a material made of glass epoxy resin. As compared with the ceramic material board, the board main body 401 has a value close to the thermal expansion coefficient of the thermoplastic resin molding the housing 302. Therefore, stress caused by a difference in thermal expansion coefficient can be reduced when insert molding is performed on the housing 302, and distortion of the circuit board 400 can be reduced.

The circuit unit is configured by mounting electronic components such as an LSI 414, a microcomputer 415, a power supply regulator 416, and a chip component 417 such as a resistance and a capacitor on a circuit wiring, not shown.

As shown in FIG. 7E, a recessed unit 402a into which the LSI 414 is fitted is formed in a recessed manner on the front surface of the board main body 401. The recessed unit 402a can be formed by subjecting the board main body 401 to laser processing. The board main body 401 made of the glass epoxy resin is easier to process than the main body made of ceramic and the recessed unit 402 can be easily provided. The recessed unit 402 has a depth such that the front surface of the LSI 414 is flush with the front surface of the board main body 401. By making the front surface of the LSI 414 and the front surface of the board main body 401 to be the same as each other in this manner, wire bonding for connecting the LSI 414 and the board main body 401 with the gold wire 411 becomes easy, and the circuit board 400 can be easily manufactured. The LSI 414 can be provided directly on the front surface of the board main body 401 as shown in FIG. 7F, for example. With such a structure, the synthetic resin material 419 covering the LSI 414 protrudes more greatly, but the processing for forming the recessed unit 402 in the board main body 401 becomes unnecessary and manufacturing can be simplified.

The protrusion unit 403 is disposed in the first sub-passage 305 when the circuit board 400 is insert molded in the housing 302, and the measurement flow path surface 430 which is the front surface of the protrusion unit 403 is placed in the flow direction of the measurement target gas 30. In the measurement flow path surface 430 of the protrusion unit 403, the flow rate detection unit 602 is provided. The flow rate detection unit 602 performs heat transfer with the measurement target gas 30, measures the state of the measurement target gas 30, for example, the flow rate of measurement target gas 30, and outputs an electric signal representing the flow rate flowing through the main passage 124. In order for the flow rate detection unit 602 to measure the state of the measurement target gas 30 with high accuracy, it is desirable that the gas flowing in the vicinity of the measurement flow path surface 430 is a laminar flow and less disordered. Therefore, it is desirable that the front surface of the flow rate detection unit 602 and the surface of the measurement flow path surface 430 are flush with each other or the difference is equal to or smaller than a predetermined value.

As shown in FIG. 7G, a recessed unit 403a is formed in a recessed manner on the front surface of the measurement flow path surface 430, and the flow rate detection unit 602 is fitted therein. The recessed unit 403a can also be formed by laser processing. The recessed unit 403a has a depth such that the front surface of the flow rate detection unit 602 is flush with the front surface of the measurement flow path surface 430. The flow rate detection unit 602 and its wiring portion are covered with a synthetic resin material 418 to prevent electrolytic corrosion due to adhesion of salt water.

On the back surface of the board main body 401, two pressure sensors 421A and 421B and one temperature and humidity sensor 422 are provided. The two pressure sensors 421A and 421B are arranged in a row separated into an upstream side and a downstream side. The temperature and humidity sensor 422 is arranged on the upstream side of the pressure sensor 421B. These two pressure sensors 421A and 421B and one temperature and humidity sensor 422 are arranged in the sensor chamber Rs. In the example shown in FIG. 7C, the case of having two pressure sensors 421A and 421B and one temperature and humidity sensor 422 has been described, but only the pressure sensor 421B and the temperature and humidity sensor 422 may be provided, or only the temperature and humidity sensor 422 may be provided.

In the circuit board 400, the second sub-passage 306 is arranged on the back surface side of the board main body 401. Therefore, the measurement target gas 30 passing through the second sub-passage 306 can cool the entire board main body 401.

4.2 Structure of Temperature Detection Unit 451

The temperature detection unit 451 is provided at the edge of the upstream side of the base unit 402 and at the corner of the protrusion unit 403. The temperature detection unit 451 constitutes one of detection units for detecting the physical quantity of the measurement target gas 30 flowing through the main passage 124, and is provided in the circuit board 400. The circuit board 400 has a protrusion unit 450 protruding from the second sub-passage entrance 306a of the second sub-passage 306 toward upstream of the measurement target gas 30. The temperature detection unit 451 has a chip type temperature sensor 453 provided on the back surface of the circuit board 400 as a protrusion unit 450. The temperature sensor 453 and its wiring portion are covered with a synthetic resin material and prevent electrolytic corrosion due to adhesion of salt water.

For example, as shown in FIG. 3B, in the central part of the measurement unit 331 provided with the second sub-passage entrance 306a, the upstream side external wall 336 in the measurement unit 331 constituting the housing 302 is recessed toward the downstream side. From the dent-shaped upstream side external wall 336, the protrusion unit 450 of the circuit board 400 protrudes toward the upstream side. The distal end of the protrusion unit 450 is arranged at a position more recessed than the surface of the most upstream side of the upstream side external wall 336. The temperature detection unit 451 is provided in the protrusion unit 450 on the back surface of the circuit board 400, and more specifically, provided in the protrusion unit 450 so as to face the second sub-passage 306.

Since the second sub-passage entrance 306a is formed on the downstream side of the temperature detection unit 451, the measurement target gas 30 flowing from the second sub-passage entrance 306a to the second sub-passage 306 comes into contact with the temperature detection unit 451, and then flows to the second sub-passage entrance 306a, and when the measurement target gas 30 comes into contact with the temperature detection unit 451, the temperature is detected. The measurement target gas 30 in contact with the temperature detection unit 451 directly flows from the second sub-passage entrance 306a to the second sub-passage 306, and passes through the second sub-passage 306, and then the measurement target gas 30 is discharged from the second sub-passage exit 306b to the main passage 123.

4.4 Fixing of Circuit Board 400 by Resin Molding Process and Effects Thereof

The hatched portion in FIG. 8A indicates the fixing surface 432 and the fixing surface 434 for covering the circuit board 400 with the thermoplastic resin used in the resin molding process in order to fix the circuit board 400 to the housing 302 in the resin molding process. It is important that the relationship with the shape of the sub-passage and the flow rate detection unit 602 provided on the measurement flow path surface 430 and the measurement flow path surface 430 is maintained with high accuracy so as to be a predetermined relationship.

In the resin molding process, simultaneously with molding the sub-passage, the circuit board 400 is fixed to the housing 302 which molds the sub-passage. Therefore, the relationship between the sub-passage, the measurement flow path surface 430, and the flow rate detection unit 602 can be maintained with extremely high accuracy. More specifically, since the circuit board 400 is fixed to the housing 302 in the resin molding process, it is possible to position and fix the circuit board 400 with high precision in a mold for molding the housing 302 having the sub-passage. By injecting high temperature thermoplastic resin into this mold, the sub-passage is molded with high precision and the circuit board 400 is fixed with high accuracy. Therefore, errors and variations occurring in each circuit board 400 can be suppressed to very small values. As a result, measurement accuracy of the circuit board 400 can be greatly improved.

In this embodiment, the outer circumference of the base unit 402 of the board main body 401 is covered with the fixing units 372 and 373 of the mold resin molding the housing 302 to make the fixing surfaces 432 and 434. In the embodiment shown in FIG. 8A, the through hole 404 is provided in the board main body 401 of the circuit board 400 as a fixing means for further strengthening fixing, and by filling the through hole 404 with the mold resin, the fixing force of the board main body 401 is increased. The through hole 404 is provided at a location fixed by the partition wall 335, and the partition wall 335 is connected to the front side and the back side via the through hole 404.

The through hole 404 is preferably provided at a position corresponding to the partition wall 335. Since the mold resin is a thermoplastic resin and the board main body 401 is made of glass epoxy, the chemical bonding action is low, and it is difficult to make adhesion tightly. The partition wall 335 has a long length with respect to the width, and has a structure that is easily spread in a direction away from the board main body 401. Therefore, by providing the through hole 404 at a position corresponding to the partition wall 335, the partition walls 335 sandwiching the board main body 401 can be physically coupled to each other via the through hole 404. Therefore, the circuit board 400 can be more firmly fixed to the housing 302, and a gap can be prevented from being formed between the circuit board 400 and the protrusion unit 403. Therefore, the measurement target gas 30 can be prevented from entering the circuit chamber Rc through the gap between the partition wall 335 and the protrusion unit 403, and the inside of the circuit chamber Rc can be completely sealed.

Figure 8B:
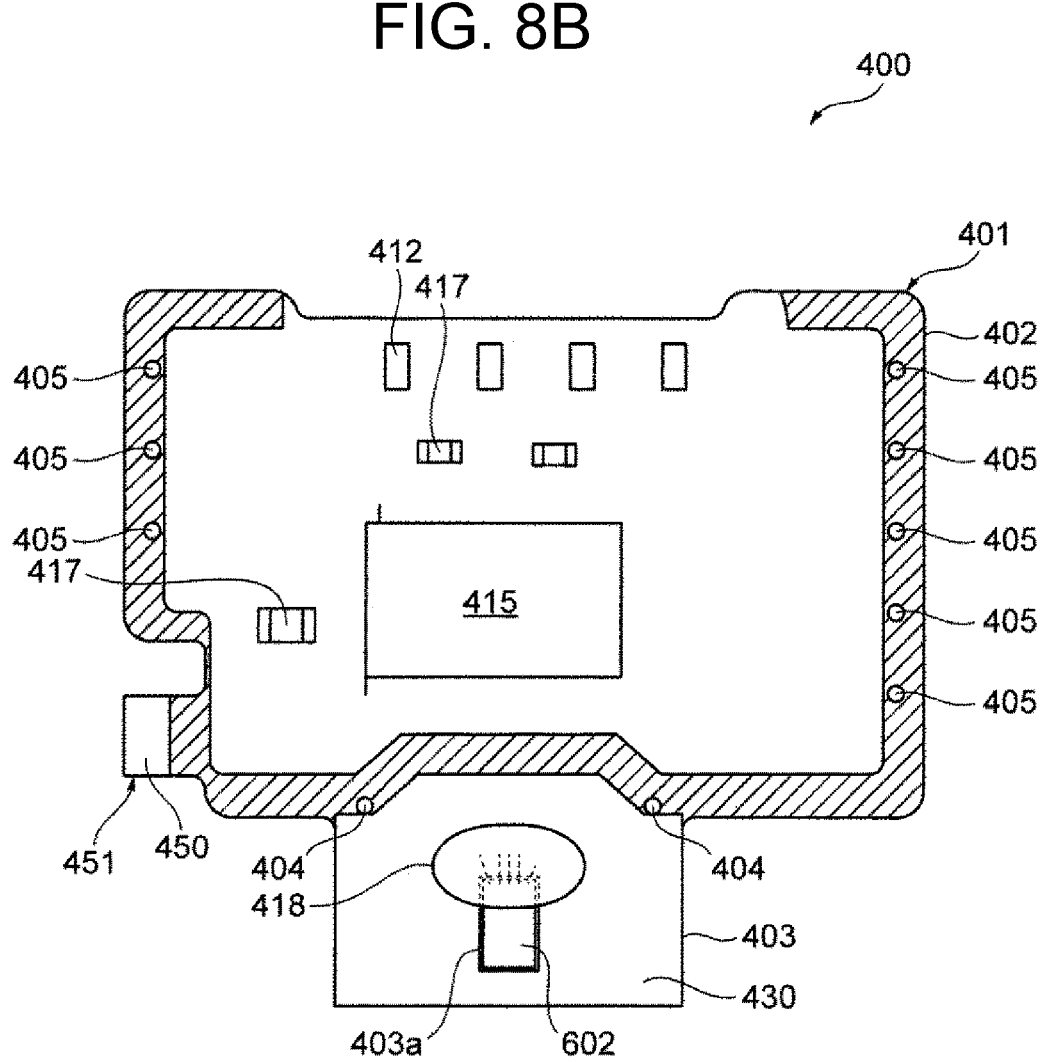
FIG. 8B is a front view showing another embodiment of a circuit board.

In the embodiment shown in FIG. 8B, in addition to the through hole 404, round hole shaped through holes 405 are provided on each of the edge side of the upstream side and the edge side of the downstream side of the base unit 402, and the through hole 405 is filled with a mold resin to further increase the fixing force of the board main body 401. The edge side of the upstream side and the edge side of the downstream side of the base unit 402 are sandwiched from both sides in the thickness direction by the fixing units 372 and 373, and the front side and the back side are further connected via the through hole 405. Therefore, the circuit board 400 can be more firmly fixed to the housing 302.

Figure 8C:
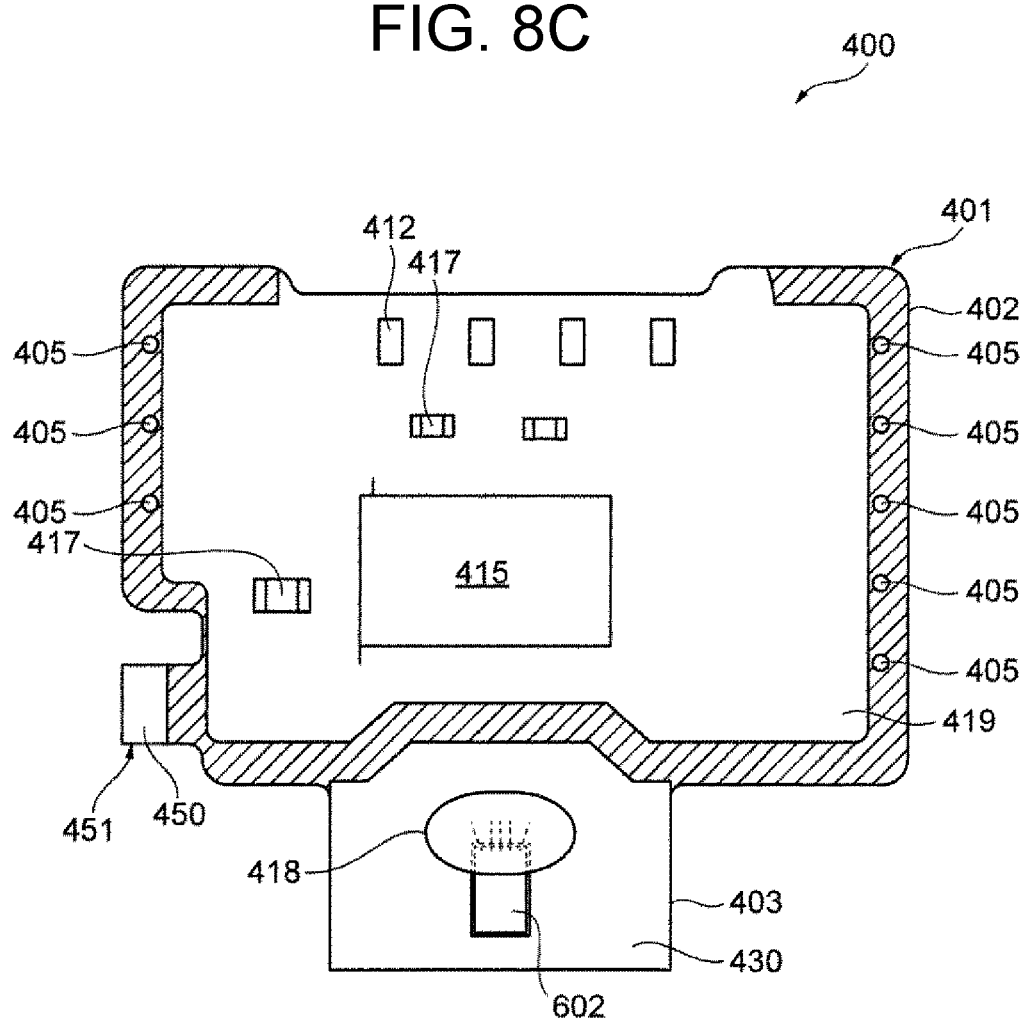
FIG. 8C is a front view showing another embodiment of a circuit board.

It is preferable to provide the through hole 404 in the partition wall 335, but when the partition wall 335 is fixed to the board main body 401 with a predetermined fixing force, the through hole 404 can be omitted. In the embodiment shown in FIG. 8C, the through hole 404 is omitted, and the through holes 405 are provided on the edge side of the upstream side and the edge side of the downstream side of the base unit 402. With such a configuration, the board main body 401 of the circuit board 400 can be firmly fixed to the housing 302.

Figure 8D:
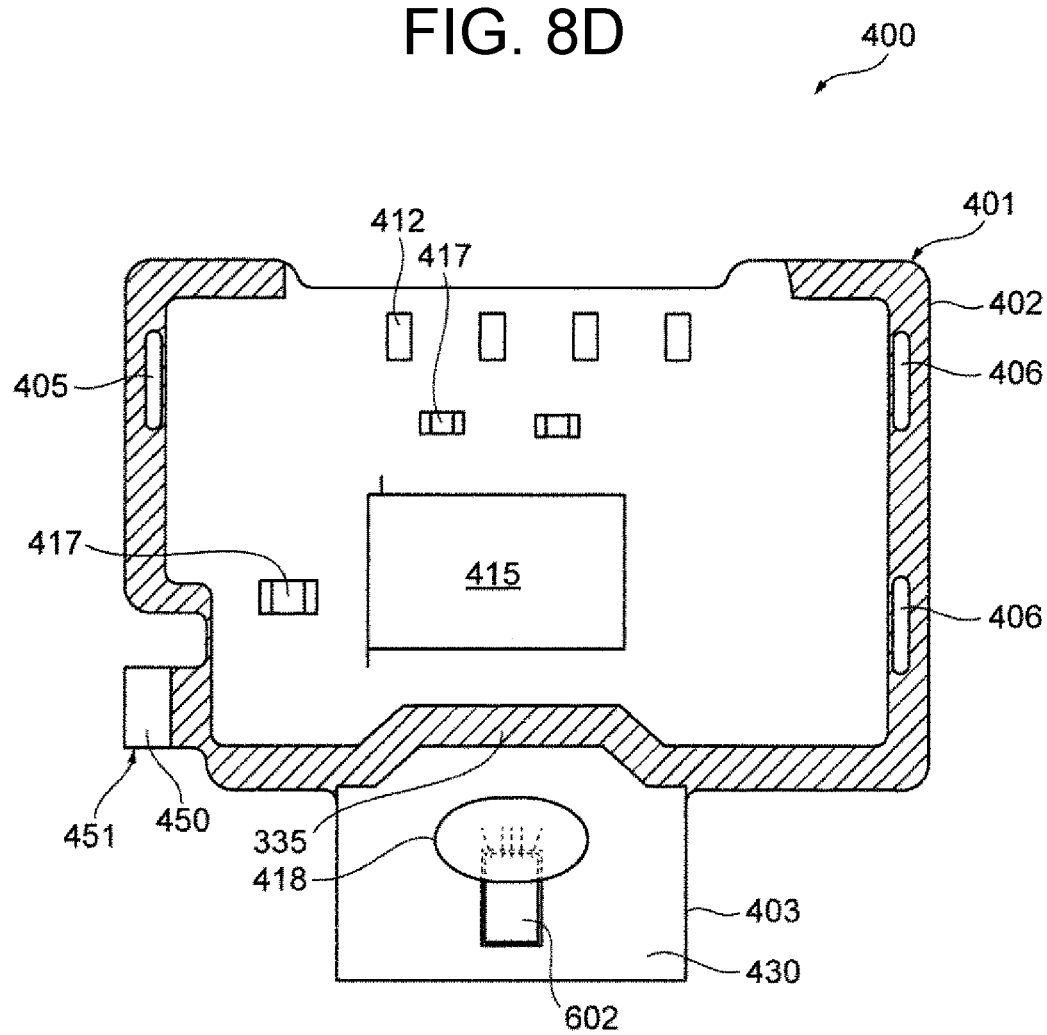
FIG. 8D is a front view showing another embodiment of a circuit board.

The through hole is not limited to the round hole shape, but it may be an elongated through hole 406 as shown in FIG. 8D, for example. In the present embodiment, the long hole shaped through hole 406 is provided so as to extend along the edge side of the upstream side and the edge side of the downstream side of the base unit 402. The through hole 406 has a larger amount of resin connecting the front side and the back side of the measurement unit 331 as compared with the through hole 406, so that a higher fixing force can be obtained.

Figure 8E:
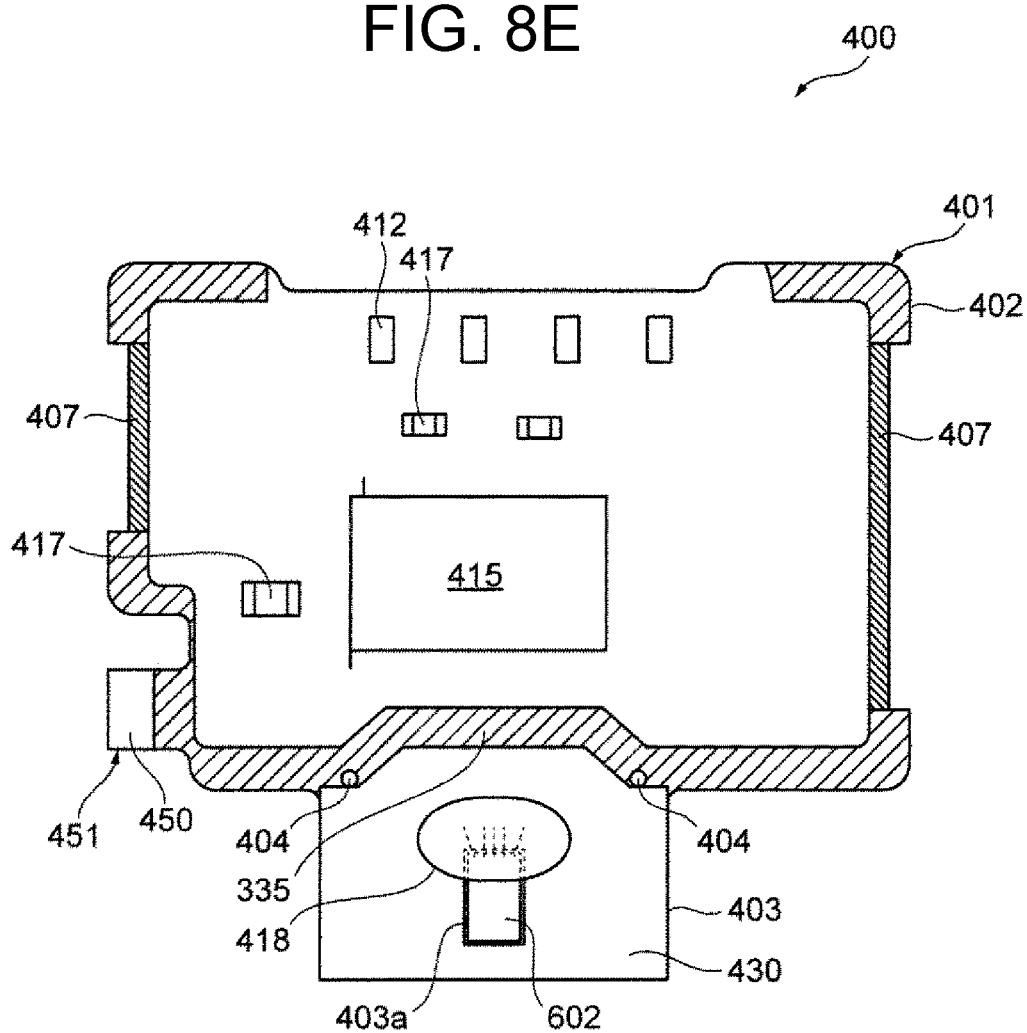
FIG. 8E is a front view showing another embodiment of a circuit board.
Figure 8F:
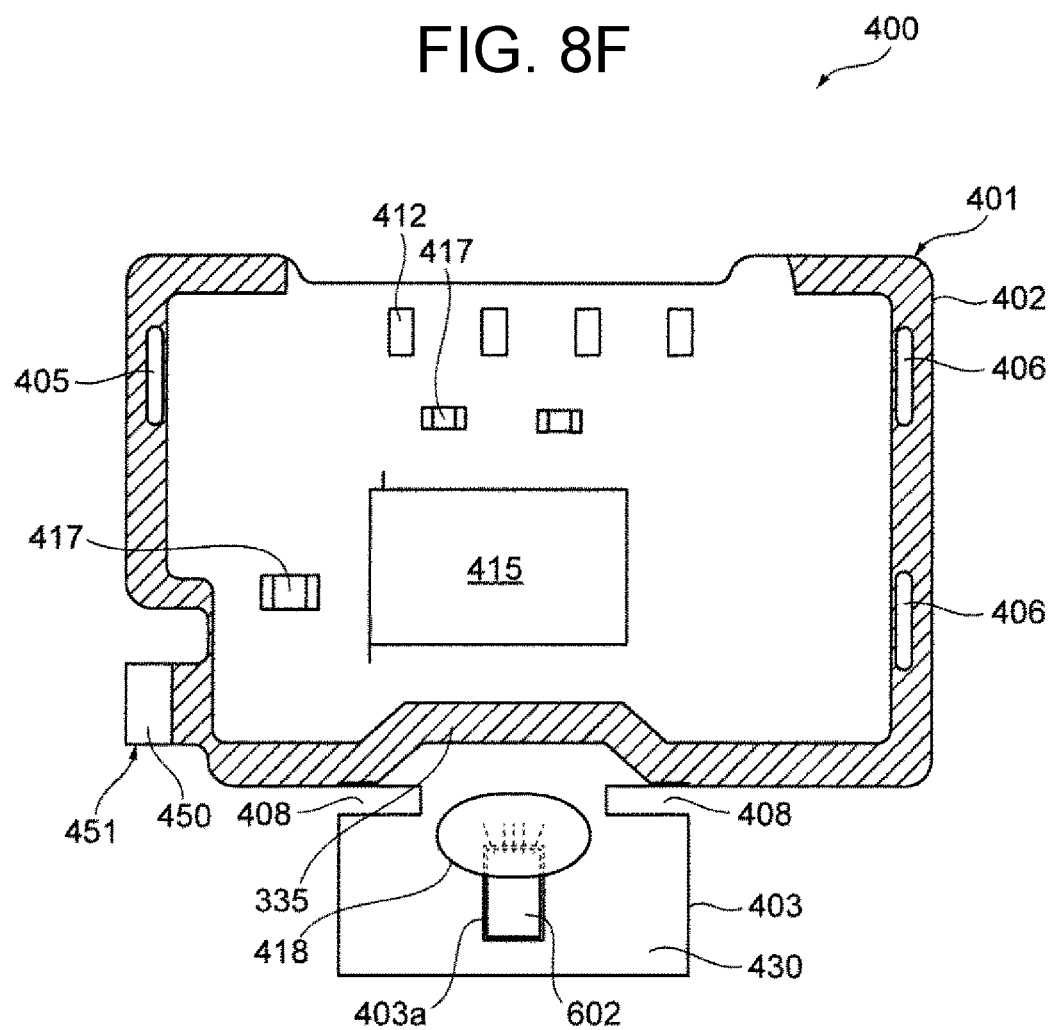
FIG. 8F is a front view showing another embodiment of a circuit board.
Figure 8G:
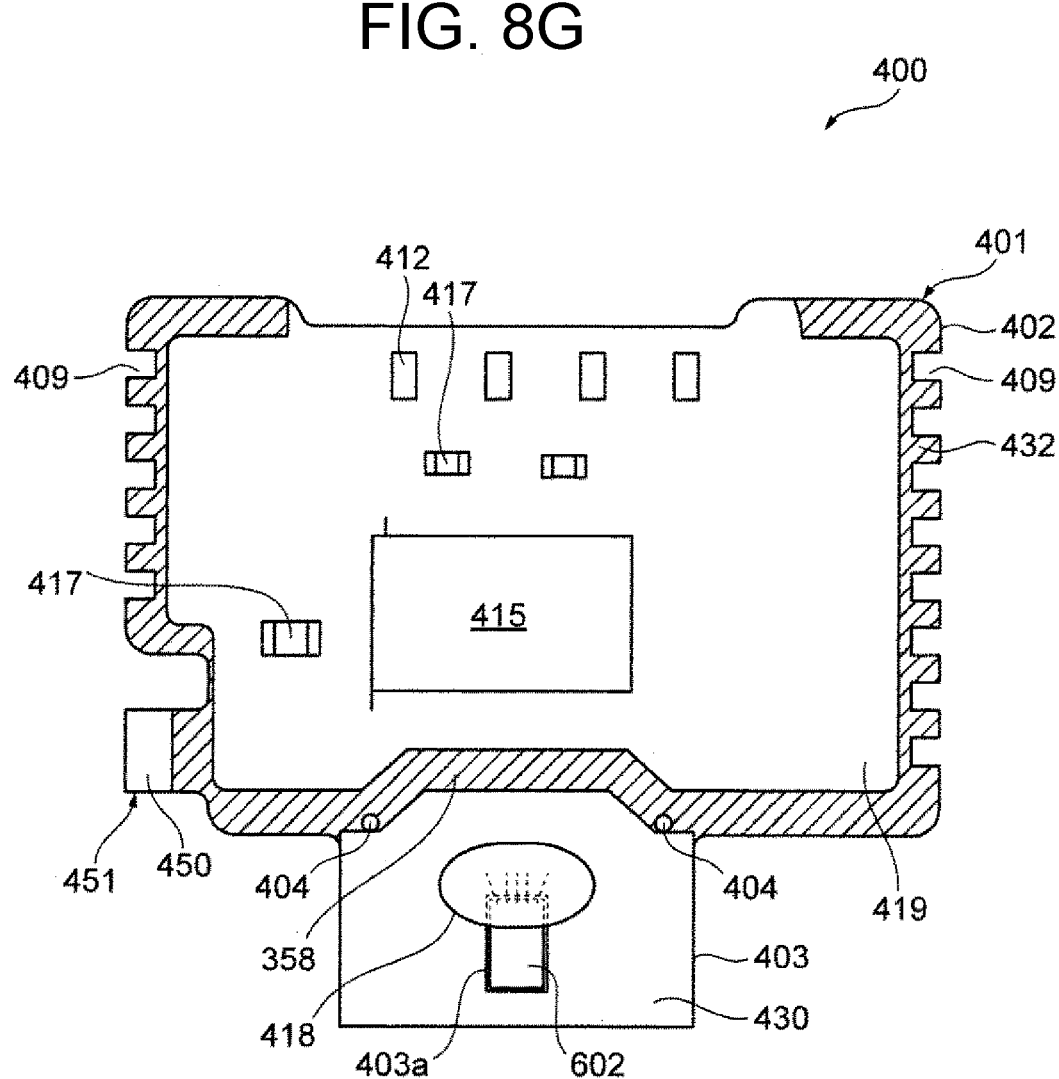
FIG. 8G is a front view showing another embodiment of a circuit board.
Figure 8H:
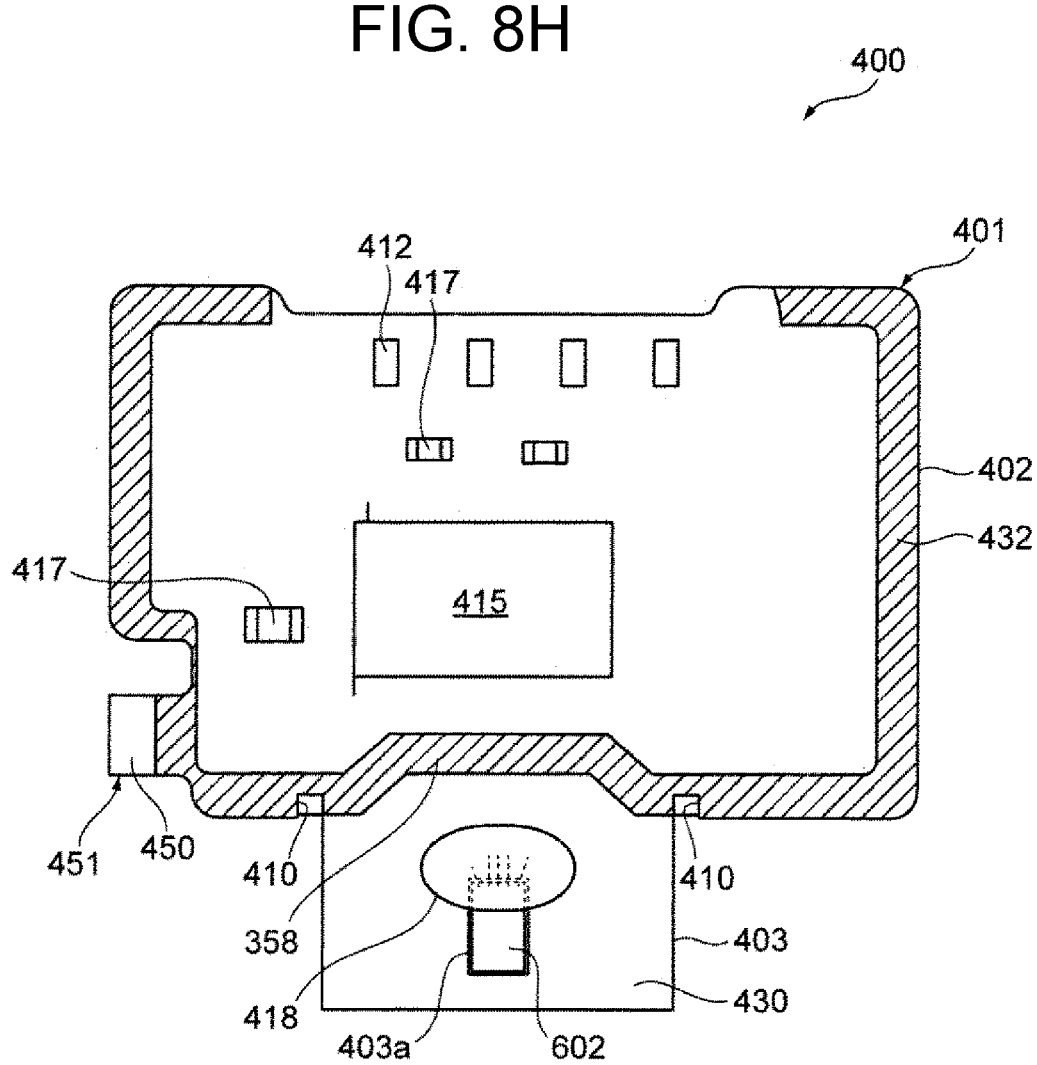
FIG. 8H is a front view showing another embodiment of a circuit board.

In each of the above-mentioned embodiments, the case of the through holes 404, 405, and 406 has been described as an example of the fixing means, but the fixing means is not limited to the through hole. For example, in the embodiment shown in FIG. 8E, a large notch portion 407 extending over its length-direction is provided in the edge side of the upstream side and the edge side of the downstream side of the base unit 402. In the embodiment shown in FIG. 8F, a notch portion 408 is provided between the base unit 402 and the protrusion unit 403. In the embodiment shown in FIG. 8G, multiple notch portions 409 are provided so as to be aligned at a predetermined interval in the edge side of the upstream side and the edge side of the downstream side of the base unit 402. In the embodiment shown in FIG. 8H, a pair of notch portions 410 cut out from both sides of the protrusion unit 403 toward the base unit 402 is provided. With these configurations, the board main body 401 of the circuit board 400 can also be firmly fixed to the housing 302.

7. Circuit Configuration of Physical Quantity Detection Device 300

7.1 Entire Circuit Configuration of Physical Quantity Detection Device 300

Figure 10A:
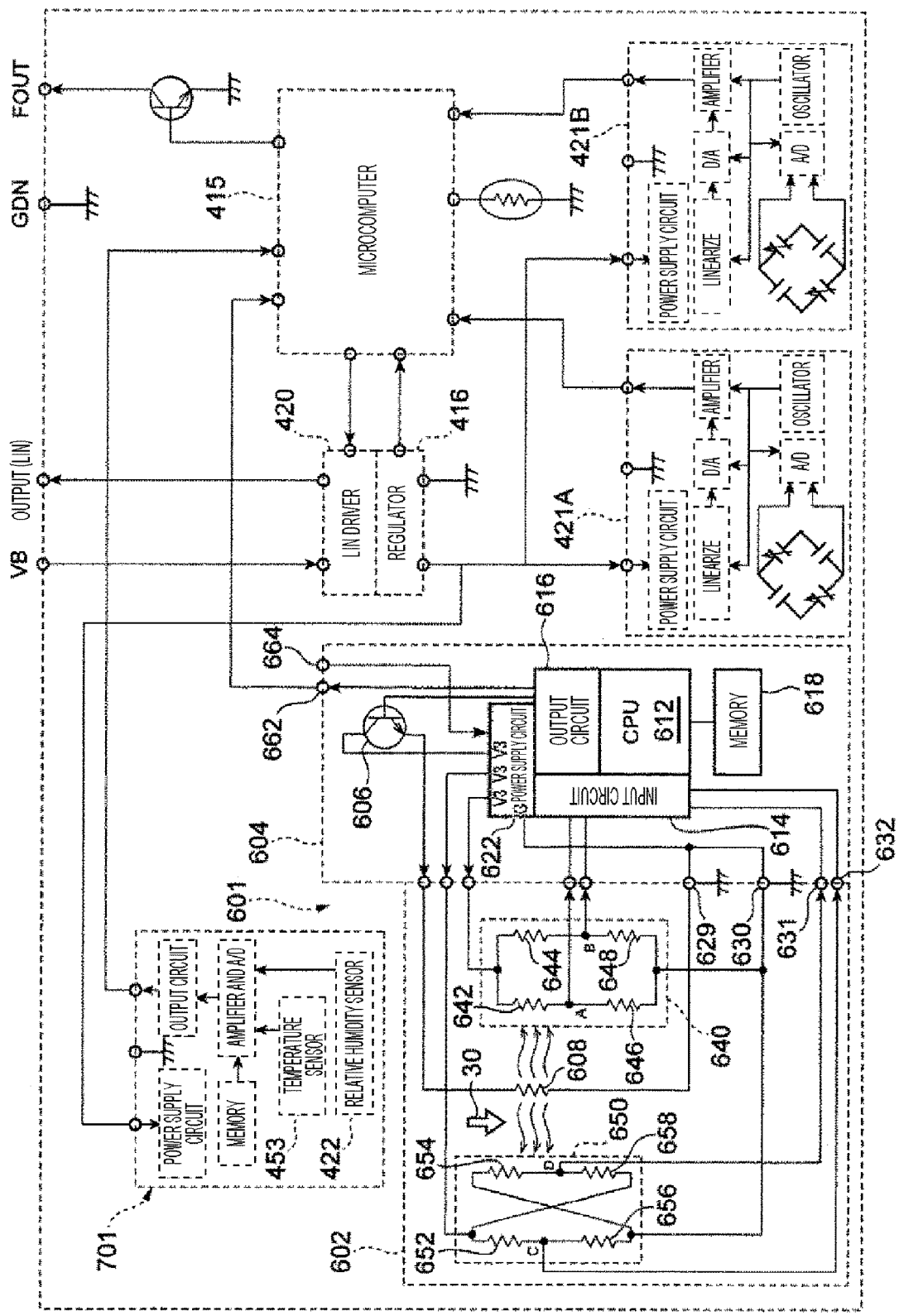
FIG. 10A is a diagram illustrating an example of a circuit configuration of a physical quantity detection device.

FIG. 10A is a circuit diagram of the physical quantity detection device 300. The physical quantity detection device 300 has a flow rate detection circuit 601 and a temperature and humidity detection circuit 701.

The flow rate detection circuit 601 includes a flow rate detection unit 602 having a heating element 608 and a processing unit 604. The processing unit 604 controls the amount of heat generated by the heating element 608 of the flow rate detection unit 602 and outputs a signal indicating the flow rate to the microcomputer 415 via the terminal 662 based on the output of the flow rate detection unit 602. In order to perform the processing, the processing unit 604 includes a Central Processing Unit (hereinafter referred to as CPU) 612, an input circuit 614, an output circuit 616, a memory 618 for holding data representing the relationship between the correction value and measured value and flow rate, and a power supply circuit 622 for supplying a constant voltage to each required circuit. ADC power is supplied to the power supply circuit 622 from an external power supply such as a vehicle battery via a terminal 664 and a ground terminal (not shown).

The flow rate detection unit 602 is provided with a heating element 608 for heating the measurement target gas 30. From the power supply circuit 622, a voltage V1 is supplied to the collector of a transistor 606 constituting the electric current supply circuit of the heating element 608, and a control signal is applied from the CPU 612 via the output circuit 616 to the base of the transistor 606, and an electric current is supplied to the heating element 608 from the transistor 606 via the terminal 624 based on the control signal. The electric current amount supplied to the heating element 608 is controlled by the control signal applied to the transistor 606 which constitutes the electric current supply circuit of the heating element 608 from the CPU 612 via the output circuit 616. The processing unit 604 controls the heat generation amount of the heating element 608 so that the temperature of the measurement target gas 30 is increased by a predetermined temperature, for example, 100 degrees Celsius, from the initial temperature by being heated by the heating element 608.

The flow rate detection unit 602 has a heat generation control bridge 640 for controlling the heat generation amount of the heating element 608 and a flow rate detection bridge 650 for measuring the flow rate. A constant voltage V3 is supplied from the power supply circuit 622 to one end of the heat generation control bridge 640 via the terminal 626. The other end of the heat generation control bridge 640 is connected to the ground terminal 630. A constant voltage V2 is supplied from the power supply circuit 622 to one end of the flow rate detection bridge 650 via the terminal 625. The other end of the flow rate detection bridge 650 is connected to the ground terminal 630.

The heat generation control bridge 640 has a resistance 642 which is a temperature measuring resistance member whose resistance value varies based on the temperature of the heated measurement target gas 30. The resistance 642, the resistance 644, the resistance 646, and the resistance 648 constitute the bridge circuit. The potential difference between the intersection A of the resistance 642 and the resistance 646 and the intersection B of the resistance 644 and the resistance 648 is input to the input circuit 614 through the terminal 627 and the terminal 628. The CPU 612 controls the electric current supplied from the transistor 606 so that the potential difference between the intersection A and the intersection B becomes a predetermined value (i.e., zero volts in this embodiment), thereby setting the heat generation amount of the heating element 608. The flow rate detection circuit 601 described in FIG. 10A heats the measurement target gas 30 with the heating element 608 so that the temperature of the measurement target gas 30 is higher by a certain temperature (for example, always 100 degrees Celsius) with respect to the original temperature of the measurement target gas 30. In order to perform this heating control with high accuracy, the resistance value of each resistance constituting the heat generation control bridge 640 is set so that the potential difference between the intersection A and the intersection B becomes zero volts when the temperature of the measurement target gas 30 heated by the heating element 608 rises by a certain temperature (for example, always 100 degrees Celsius) with respect to the initial temperature. Therefore, in the flow rate detection circuit 601, the CPU 612 controls the supply electric current to the heating element 608 so that the potential difference between the intersection A and the intersection B becomes zero volts.

The flow rate detection bridge 650 is constituted by four resistance temperature detectors, i.e., a resistance 652, a resistance 654, a resistance 656, and a resistance 658. These four resistance temperature detectors are arranged along the flow of measurement target gas 30. The resistance 652 and the resistance 654 are arranged on the upstream side in the flow path of the measurement target gas 30 with respect to the heating element 608. The resistance 656 and the resistance 658 are arranged on the downstream side in the flow path of the measurement target gas 30 with respect to the heating element 608. In order to improve the measurement accuracy, the resistance 652 and the resistance 654 are arranged so that the distances to the heating element 608 are substantially equal to each other. The resistance 656 and the resistance 658 are arranged such that distances to the heating element 608 are substantially equal to each other.

The potential difference between the intersection C of the resistance 652 and the resistance 656 and the intersection D of the resistance 654 and the resistance 658 is input to the input circuit 614 via the terminal 631 and the terminal 632. In order to increase the measurement accuracy, each resistance of the flow rate detection bridge 650 is set so that the potential difference between the intersection C and the intersection D becomes zero when, for example, the flow of the measurement target gas 30 is zero. Therefore, in the state where the potential difference between the intersection C and the intersection D is, for example, zero volts, the CPU 612 outputs an electric signal, indicating that the flow rate of the main passage 124 is zero, from the terminal 662 based on the measurement result that the flow rate of the measurement target gas 30 is zero.

When the measurement target gas 30 flows in the direction of the arrow in FIG. 10A, the resistance 652 and the resistance 654 disposed on the upstream side are cooled by the measurement target gas 30, and the resistance 656 and the resistance 658 located on the downstream side of the measurement target gas 30 are warmed by the measurement target gas 30 warmed by the heating element 608, and the temperature of these resistance 656 and resistance 658 rises. Therefore, a potential difference occurs between the intersection C and the intersection D of the flow rate detection bridge 650, and the potential difference is input to the input circuit 614 via the terminal 631 and the terminal 632. Based on the potential difference between the intersection C and the intersection D of the flow rate detection bridge 650, the CPU 612 searches for data representing the relationship between the potential difference stored in the memory 618 and the flow rate of the main passage 124, and derives the flow rate of main passage 124. An electric signal representing the flow rate of the main passage 124 obtained in this manner is output via the terminal 662. Note that the terminal 664 and the terminal 662 shown in FIG. 10A have new reference numbers. However, the terminal 664 and the terminal 662 are included in the connection terminal 412 shown in FIG. 8A described above.

The memory 618 stores data indicating the relationship between the potential difference between the intersection C and the intersection D and the flow rate of the main passage 124, and stores correction data for reducing the measurement error such as variation, which is obtained based on the measured value of gas after production of the circuit board 400.

The temperature and humidity detection circuit 701 includes an input circuit such as an amplifier and A/D which input a detection signal from the temperature sensor 453 and the temperature and humidity sensor 422, an output circuit, a memory that holds data representing the relationship between the absolute humidity and the temperature and the correction values, and a power supply circuit 622 supplying a constant voltage to each required circuit. The signal output from the flow rate detection circuit 601 and the temperature and humidity detection circuit 701 is input to the microcomputer 415. The microcomputer 415 has a flow rate calculation unit, a temperature calculation unit, and an absolute humidity calculation unit. The microcomputer 415 calculates the flow rate, temperature, absolute humidity which are the physical quantities of the measurement target gas 30 based on the signal, and outputs them to the ECU 200.

The physical quantity detection device 300 and the ECU 200 are connected via a communication cable, and communication using a digital signal is performed according to a communication standard such as SENT, LIN, or CAN. In the present embodiment, a signal is input from the microcomputer 415 to the LIN driver 420, and LIN communication is performed from the LIN driver 420. Information output from the LIN driver of the physical quantity detection device 300 to the ECU 200 is superimposed and output by digital communication using a single or two-wire communication cable.

The absolute humidity calculation unit of the microcomputer 415 calculates the absolute humidity based on the information of the relative humidity output from the temperature and humidity sensor 422 and the temperature information and corrects the absolute humidity based on the error. The corrected absolute humidity calculated by the absolute humidity calculation unit is used for various engine operation control in the control unit 62 of the ECU 18. Further, the ECU 18 can directly use information about total error for various engine operation controls.

Figure 10B:
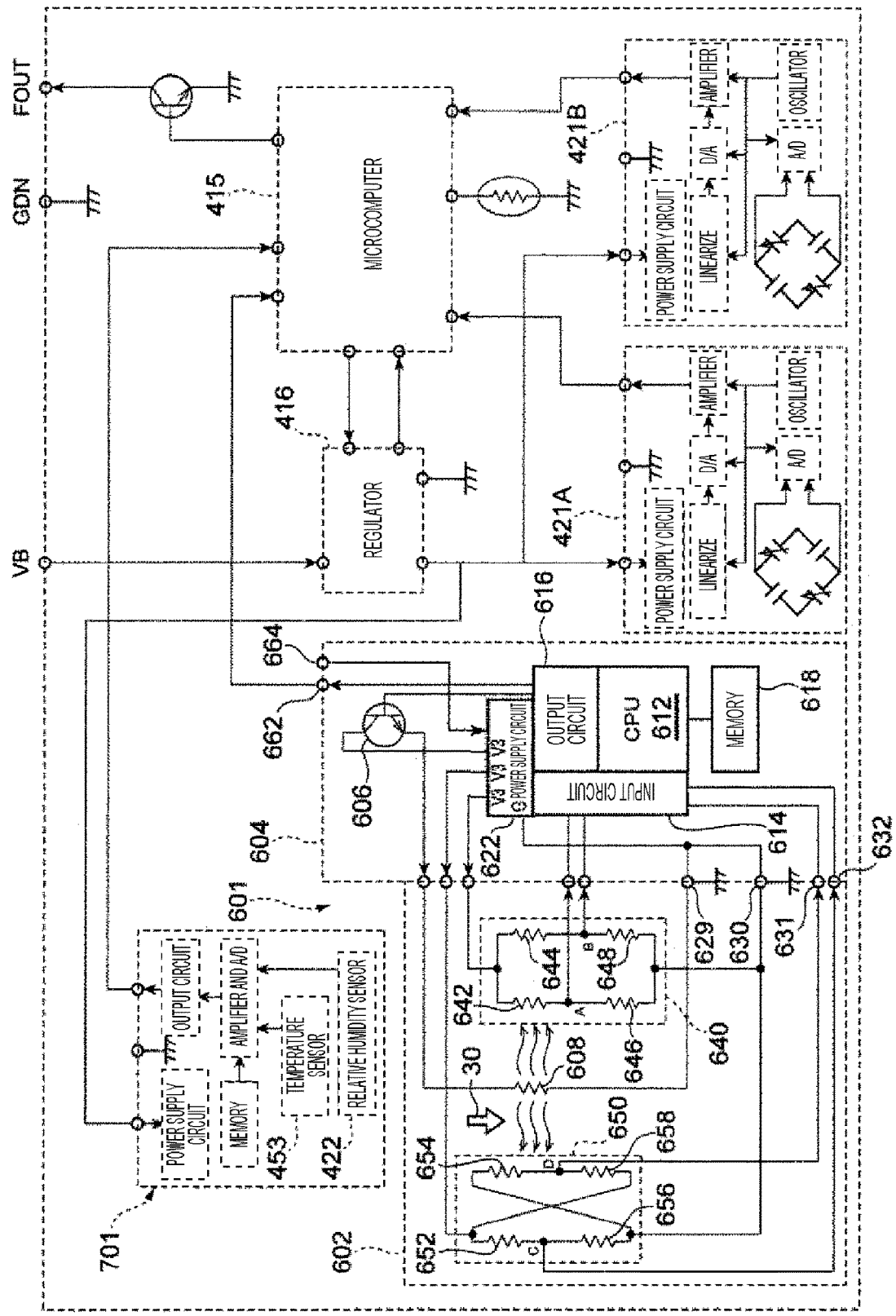
FIG. 10B is a diagram for explaining another embodiment of a circuit configuration of a physical quantity detection device.

In the above-described embodiment shown in FIGS. 10A and 10B, the physical quantity detection device 300 has the LIN driver 420 and the LIN communication is performed, but the present invention is not limited thereto. Alternatively, as shown in FIG. 10B, direct communication with microcomputer 415 may be performed without using LIN communication.

4.5 Component Arrangement on Circuit Board 400

Figure 11A:
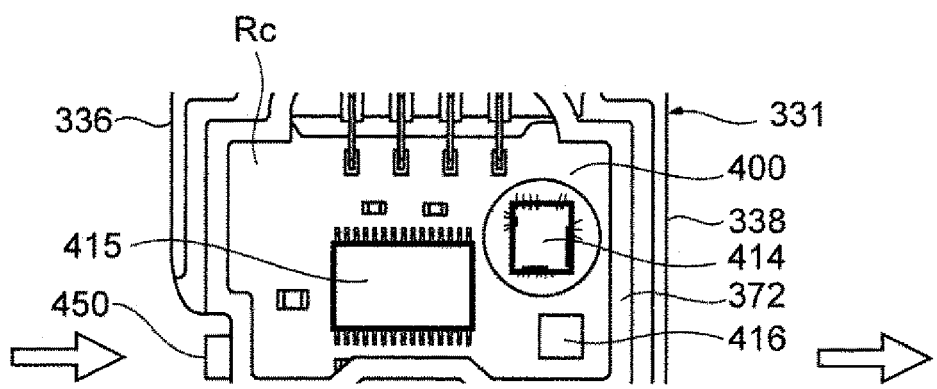
FIGS. 11A and 11B are views for explaining a component arrangement of the circuit board of the physical quantity detection device.
Figure 11B:
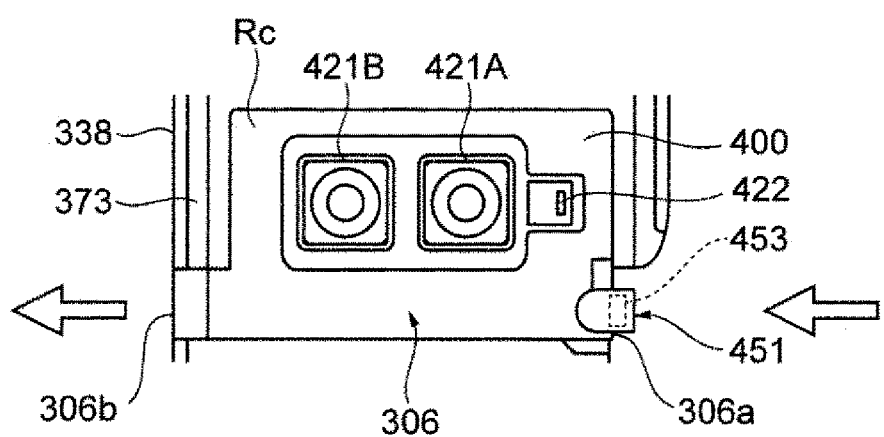

FIGS. 11A and 11B show a mode showing the present invention. FIG. 11A is a front view of the circuit board. FIG. 11B is a back surface diagram of the circuit board.

On the back surface of the circuit board 400, a second sub-passage 306 is formed to extend between the second sub-passage entrance 306a and the second sub-passage exit 306b to take in the measurement target gas 30 flowing through the main passage 124. A temperature sensor 453 is provided in the protrusion unit 450. The temperature sensor 453 directly comes into contact with the measurement target gas 30 and detects the intake temperature. The temperature and humidity sensor 422 is mounted on the back surface of the circuit board 400 to directly come into contact with the measurement target gas 30 flowing in from the second sub-passage 306 and detects the intake temperature.

In the present embodiment, since the signal transmission from the physical quantity detection device 300 to the ECU is performed in LIN communication, the battery voltage is supplied to the physical quantity detection element 300. The power supply regulator 416 steps down the battery voltage from 12 V to 5 V used for normal sensor drive. Therefore, the heat generation by the power supply regulator 416 becomes large, and the power supply regulator 416 has the maximum heat generation amount on the circuit board 400. The heat is transferred along the air flow, and therefore, the power supply regulator 416 is arranged in the air flow downstream portion from the temperature and humidity sensor 422 and the temperature sensor 453, so that the heat generated in the power supply regulator 416 is suppressed from being transmitted to the temperature and humidity sensor 422 and the temperature sensor 453 arranged in the air flow upstream portion. In order to further reduce the influence of the heat generated by the power supply regulator 416 on the temperature and humidity sensor 422 and the temperature sensor 453, it is preferable that the distance from the power supply regulator is long. By placing the power supply regulator 416 in the air flow downstream portion, it is possible to increase the distance between the temperature sensor 453 arranged near the second sub-passage entrance 306a and also to suppress the heat conduction.

In the embodiment of FIGS. 11A and 11B, the heat generation amount decreases in the following order: the power supply regulator 416, the LSI 414, and the microcomputer 415, and the power supply regulator 416, the LSI 414, and the microcomputer 415 are arranged in this order from the air flow downstream portion. Components generating large amount of heat are configured to be arranged farther from the temperature and humidity sensor 422 and the temperature sensor 453, thereby reducing heat conduction. In addition, by placing another electronic component between the temperature and humidity sensor 422 or the temperature sensor 453 and the power supply regulator 416 which is the component having the maximum heat generation amount, the effect of suppressing the heat conduction to the temperature and humidity sensor 422 and the temperature sensor 453 is also obtained.

Further, the power supply regulator 416 is disposed on the side opposite to the second sub-passage 306 with the circuit board 400 interposed therebetween. More specifically, the second sub-passage 306 is formed on the back surface which is a surface of one side where the temperature and humidity sensor 422 of the circuit board 400 and the temperature sensor 453 (an element having the intake temperature detection function) are mounted. The entire or a part of the power supply regulator 41 which is the component having the maximum heat generation amount is arranged on the front surface which is a surface of the other side of the circuit board 400 and is at the position on the opposite side of the second sub-passage 306 with the circuit board 400 interposed therebetween. For this reason, the flow velocity is high within the hermetically sealed circuit chamber Rc, the heat generated by the power supply regulator 416 is transmitted to the back surface of the board main body 401, and the effect of dissipating the heat with the measurement target gas 30 passing through the second sub-passage 306 is improved.

In the present embodiment, the circuit board 400 is molded integrally with the housing 302. On the other hand, conventionally, the circuit board was fixed on the metal base with an adhesive. Therefore, the metal base functioned as a heat sink, enhancing the effect of dissipating the heat generated in the circuit board to the surroundings. In the present embodiment, the heat affecting the temperature and humidity sensor 422 and the temperature sensor 453 due to the heat generation of the power supply regulator 416 can be reduced by the above configuration. For this reason, the metal base can be eliminated, and both-surface-mounting of the circuit board and the integrally-molded configuration with the housing can be realized.

When installed in the intake system of the internal combustion engine, the inside of the intake pipe is heated to a high temperature by being subjected to the thermal influence emitted by the internal combustion engine. For this reason, in the state where a temperature difference is present between the temperature of the measurement target gas 30 and the temperature in the intake pipe, a heat distribution is generated inside the module, which tends to cause a deterioration in measurement accuracy. Particularly, when the temperature and humidity sensor 422 is heated to a high temperature, both the relative humidity output and the temperature output are likely to shift to a condition with low measurement accuracy, and it is desirable to arrange the temperature and humidity sensor 422 at a position where the thermal influence of the internal combustion engine can be minimized. In the sensor chamber Rs, the flow velocity is stronger at a position closer to the second sub-passage entrance 306a, and therefore, the arrangement of the temperature sensor 453 according to the present embodiment also has the effect of suppressing the heat influence from the internal combustion engine.

Although the embodiments of the present invention have been described in details above, the present invention is not limited to the above-described embodiments, but various changes and modifications may be made without departing from the spirit of the present invention as set forth in the claims. For example, the mode of operation described above has been described in details in order to explain the present invention in an easy-to-understand manner and is not necessarily limited to having all the configurations described. It is possible to replace some of the configurations of one embodiment with the configurations of another embodiment, and it is also possible to add a configuration of an embodiment to a configuration of another embodiment. Further, it is possible to add, delete, or replace some of the configurations of each embodiment with other configurations.

REFERENCE SIGNS LIST

30 measurement target gas
124 main passage
300 physical quantity detection device
302 housing
306 second sub-passage
400 circuit board
404, 405, 406 through hole
407, 408 notch portion
414 LSI
415 microcomputer
416 regulator
421A, 421B pressure sensor (third detection unit)
422 temperature and humidity sensor (second detection unit)
453 temperature sensor
602 flow rate detection unit (first detection unit)

The invention claimed is:

1. A physical quantity detection device comprising one or more intake temperature detection elements and an electronic circuit board processing an electric signal,
    wherein the one or more intake temperature detection elements and a component having a maximum heat generation amount are configured to be mounted on the same electronic circuit board,
    the one or more intake temperature detection elements are arranged on a surface of a first side of the electronic circuit board, and the component having the maximum heat generation amount is arranged on a surface of a second side of the electronic circuit board different from the first side, and
    the one or more intake temperature detection elements are arranged at an air flow upstream portion with respect to the component having the maximum heat generation amount.

2. The physical quantity detection device according to claim 1, further comprising other components having a heat generation amount mounted on the electronic circuit board, wherein, of the component having the maximum heat generation amount and other components having heat generation amounts, three components having the first to third highest heat generation amounts are arranged, from air flow downstream, in a descending order of the heat generation amount.

3. The physical quantity detection device according to claim 2, wherein the three components having the first to third highest heat generation amounts are a power supply regulator, an LSI, and a microcomputer, in the descending order of the heat generation amount.

4. The physical quantity detection device according to claim 1, wherein at least one of the one or more intake temperature detection elements has a humidity detection function.

5. The physical quantity detection device according to claim 1, wherein a board main body of the electronic circuit board is made of a material made of glass epoxy resin.

6. The physical quantity detection device according to claim 1, wherein an independent sub-passage for taking in a measurement target gas passing through a main passage is formed on the surface of the first side where the one or more intake temperature detection elements of the electronic circuit board are mounted, and
    an entire or a part of the component having the maximum heat generation amount is arranged at a position on an opposite side of the sub-passage with the electronic circuit board interposed therebetween.

* * * * *